(12) United States Patent
Francke et al.

(10) Patent No.: US 12,715,749 B2
(45) Date of Patent: Aug. 25, 2026

(54) AUTOMATIC OR SEMI-AUTOMATIC CLEAN-IN-PLACE SYSTEM AND METHOD OF USING SAME

(71) Applicant: SUBD ApS, Hvidovre (DK)

(72) Inventors: Kenneth Peter Kolind Francke, Copenhagen (DK); Finn Peder Jegård, Brøndby Strand (DK); Christian Jovan Andonovski, Ballerup (DK); Jacob Skjøt-Pedersen, Farum (DK)

(73) Assignee: SUBD ApS, Hvidovre (DK)

( * ) Notice: Subject to any disclaimer, the term of this patent is extended or adjusted under 35 U.S.C. 154(b) by 172 days.

(21) Appl. No.: 18/701,069

(22) PCT Filed: Oct. 10, 2022

(86) PCT No.: PCT/DK2022/050212
§ 371 (c)(1),
(2) Date: Apr. 12, 2024

(87) PCT Pub. No.: WO2023/061541
PCT Pub. Date: Apr. 20, 2023

(65) Prior Publication Data

US 2024/0343548 A1 Oct. 17, 2024

(30) Foreign Application Priority Data

Oct. 13, 2021 (DK) ........................... PA 2021 70508

(51) Int. Cl.
*B67D 1/07* (2006.01)
*A61L 2/183* (2026.01)
(Continued)

(52) U.S. Cl.
CPC ................ *B67D 1/07* (2013.01); *A61L 2/183* (2013.01); *A61L 2/24* (2013.01); *A61L 2/26* (2013.01);
(Continued)

(58) Field of Classification Search
CPC . B67D 1/07; A01J 7/022; B08B 9/032; B08B 9/0321; B08B 9/0323; B08B 9/0325; B08B 9/0328
See application file for complete search history.

(56) References Cited

U.S. PATENT DOCUMENTS 4,582,226 A 4/1986 Doak
5,762,096 A 6/1998 Mirabile
(Continued)

FOREIGN PATENT DOCUMENTS

GB 2517709 3/2015
WO 02/100766 12/2002

OTHER PUBLICATIONS

International Search Report and Written Opinion for International PCT Patent Application No. PCT/DK2022/050212 mailed Jan. 9, 2023 (10 pages).

*Primary Examiner* — Jennifer C Chiang
(74) *Attorney, Agent, or Firm* — Fox Rothschild LLP

(57) ABSTRACT

An automatic or semi-automatic Clean-In-Place system serves for cleaning at least one dispensing line between a take-off station and a dispensing station with dispensers at the end of dispensing lines and is operated by an electronic control system. A source of ozonated water provides ozonated water through ozonated water conduit via an ozonated water valve, and cleaning water is provide through water conduit via a water valve. A main conduit in turns receives water from the water conduit and ozonated water from the ozonated water conduit. The main conduit extends into serially arranged flow distribution units, each comprising serially arranged branch conduits on the main conduit. A second coupler is adapted to couple in fluid communication with a first coupler at the end of a dispensing line.

21 Claims, 11 Drawing Sheets

Figure 1:
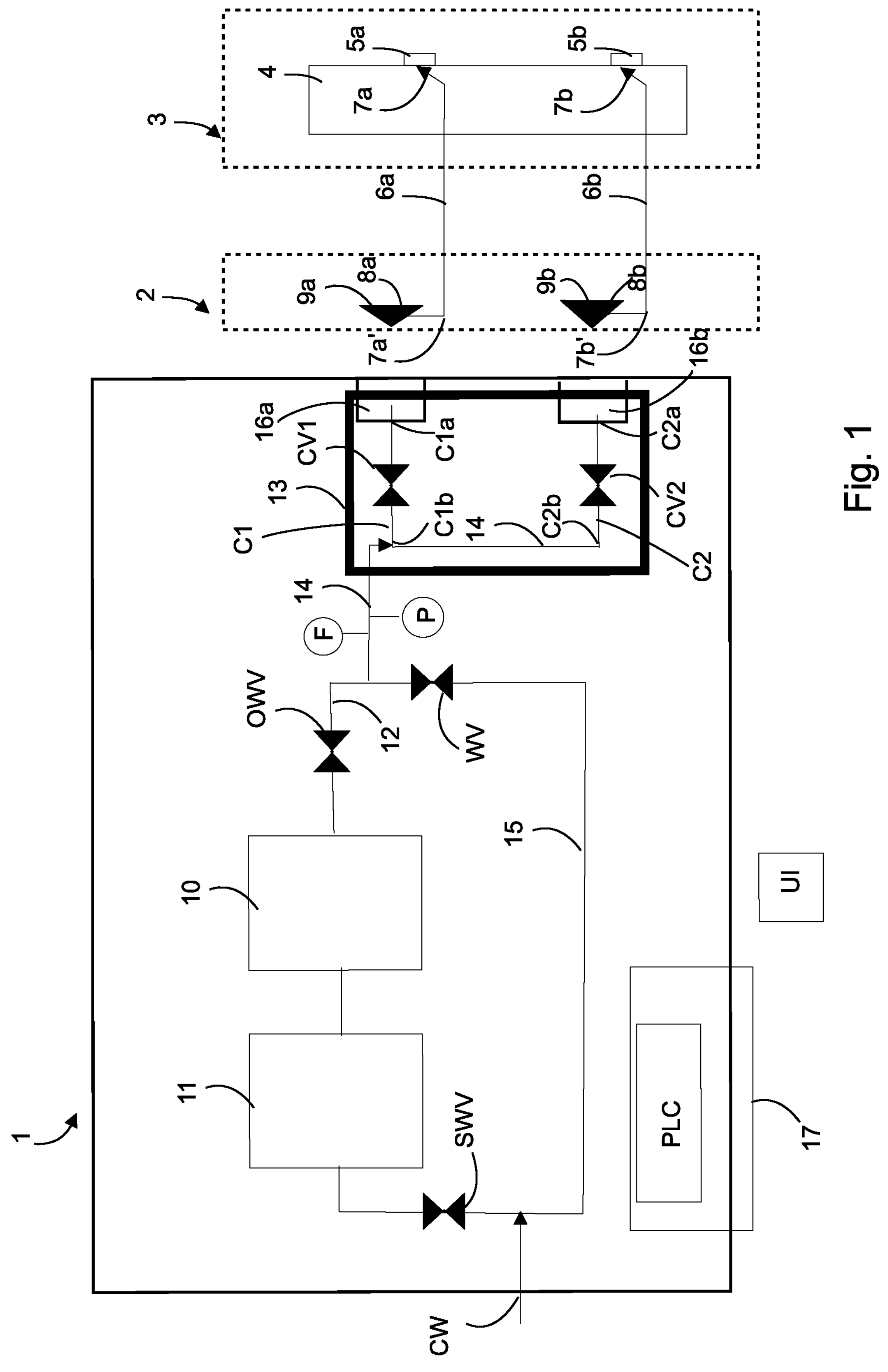

(51) Int. Cl.
*A61L 2/24* (2006.01)
*A61L 2/26* (2006.01)
*B08B 9/032* (2006.01)
*C02F 1/461* (2023.01)
*C02F 1/467* (2023.01)

(52) U.S. Cl.
CPC ........ *B08B 9/0325* (2013.01); *C02F 1/46104* (2013.01); *C02F 1/4672* (2013.01); *A61L 2202/11* (2013.01); *A61L 2202/14* (2013.01); *A61L 2202/15* (2013.01); *A61L 2202/17* (2013.01); *B08B 2209/032* (2013.01); *C02F 2201/004* (2013.01); *C02F 2201/005* (2013.01)

(56) References Cited

U.S. PATENT DOCUMENTS

2004/0245281 A1* 12/2004 Oke ...................... B08B 9/0327
222/1
2022/0371874 A1* 11/2022 Hartmann ............ B67D 1/0855

* cited by examiner

AUTOMATIC OR SEMI-AUTOMATIC CLEAN-IN-PLACE SYSTEM AND METHOD OF USING SAME

CROSS REFERENCE TO RELATED APPLICATIONS

This application is a U.S. National Phase Application of PCT International Application No. PCT/DK2022/050212, filed on Oct. 10, 2022, which is an international application of and claims the benefit of priority to Danish Patent Application No. PA 2021 70508, filed on Oct. 13, 2021. The entire contents of these patent applications are herein incorporated by reference.

The present invention relates to an automatic or semi-automatic Clean-In-Place (CIP) system adapted for cleaning at least one dispensing line between a take-off station comprising at least one take-off receptacle and a dispensing station comprising at least one dispenser, wherein a dispensing line has a take-off end provided with a first coupler configured to couple to the take-off receptacle, and an opposite dispenser end adapted to be connected to a dispenser, wherein a source of ozonated water is connected to an ozonated water conduit, and a source of cleaning water is connected to a water conduit.

In particular the present invention concerns a Clean-In-Place method and a Clean-In-Place system for cleaning the dispensing lines of a draught beer system comprising multiple take-off receptacles in form of beer kegs and a dispensing station comprising multiple faucets arranged in a dispensing tower.

It should however be emphasized that the present invention is not limited to be used to disinfect draught beer dispensing lines. The present invention is applicable for disinfecting any kind of dispensing system, including but not limited to draught beverage and draught water dispensing systems, as well as dispensing systems in factory environment, such as tapping systems for dairy products, pharmaceutical, cosmetics, and almost any kind of fluid, liquid, viscous or creamy products.

Within the context of the present invention the term Clean-In-Place (CIP) means at least partly automated cleaning of the interior surfaces of component including one or more of pipes and hoses, vessels, equipments, filters and associated fittings, without major disassembling of such components and substantial removing of such components from their location of use.

Beer and many other beverages contain alcohol, carbon dioxide, finished proteins, carbohydrates and many other organic compounds. Yeast and bacteria routinely enter the draught systems where they feed on these organic compounds and attach to the dispensing lines. A further issue that calls for frequent cleaning of the dispensing lines is that minerals precipitate from beer leaving deposits in dispensing lines, kegs and fixtures. Within weeks of installing a brand-new draught system, deposits begin to build up on the beer contact surfaces. Without proper cleaning, these deposits soon affect beer flavor and undermine the system's ability to pour quality beer.

Perlick's Draught Beer Reference Manual (Perlick Corporation, 8300 W. Good Hope Rd. Milwaukee, WI 53223) and the Draught Beer Quality Manual (fourth edition, ISBN 9781938469602) are published by Brewers Association, 1327 Spruce Street Boulder, CO 80302, web: https://www.brewersassociation.org/.

These references discuss the conventional ways for draught beer dispensing line cleaning by way of manual cleaning using either caustic or acidic chemicals, and recommend that a dispensing line is cleaned and maintained, preferably every 2-4 weeks, or any time a keg is changed.

The beer inside a keg will retain its full flavor about 30-45 days after tapping; however a keg's "shelf-life" is dependent on storage conditions and the brand/style of the beer; however bacteria will eventually spoil unpasteurized keg beer. Thus the intervals of which the beer kegs must be cleaned depend on many different factors.

It is explained that caustic chemicals remove organic material from the interior of the draught beer dispensing line, hardware and fittings. The removal of this buildup prevents growth of beer spoiling bacteria such as lactobacillus, pediococcus and pectinatus. A typical caustic chemical is sodium hydroxide, potassium hydroxide or a combination of both. Some caustic line cleaning solutions add EDTA or another chelating agent to help remove calcium oxalate (beer stone) from draught beer dispensing lines. Acidic chemicals can also remove inorganic materials such as calcium oxalate and calcium carbonate (water stone) from the interior of the draught beer dispensing line, hardware and fittings. Acid-based dispensing line cleaners suitable for draught beer dispensing line cleaning contain solutions of phosphoric acid, but exclude hydrochloric acid that corrodes to stainless steel, and nitric acid that is not compatible with nylon products. Both caustic and acidic chemicals are used warm at a temperature of about 26° C. and 38° C. and must remain in contact with the draught line for at least 15 minutes when solution is being re-circulated, and 20 minutes for static, or pressure pot cleaning. Due to the hazardous chemicals draught beer dispensing line cleaning should only be performed by trained personnel. Personal protection equipment including rubber gloves and eye protection must be used whenever handling such harsh cleaning chemicals. Material Safety Data Sheets must be observed to avoid rapid increase in temperature when mixing chemicals, to thereby avoid violent and dangerous spattering or eruption of the mixed chemicals.

Other line cleaning devices to be mentioned to clean draught beer dispensing lines are electrical or sonical cleaning devices, but these are not suitable substitutes for chemical line cleaning. Although some sonic cleaning devices may inhibit bacteria and yeast growth, they have little or no cleaning effect on draught beer tapping hardware and fittings.

Japanese patent application no. JP H03236850 A discloses an automatic or semi-automatic Clean-In-Place system that comprises a source of ozonated water connected to an ozonated water conduit and a source of cleaning water connected to a water conduit.

It is a main aspect of the present invention to provide an alternative system and method of cleaning and/or disinfecting one or more dispensing lines between a take-off station and a dispensing station.

It is another main aspect of the present invention to provide a system and method of cleaning and/or disinfecting one or more dispensing lines between a take-off station and a dispensing station that is/are environmentally friendly.

It is another aspect of the present invention to provide a system and method of cleaning and/or disinfecting one or more dispensing lines between a take-off station and a dispensing station with minimum human interaction.

It is another aspect of the present invention to provide a system and method of cleaning and/or disinfecting one or more dispensing lines between a take-off station and a dispensing station that reduces staff work.

It is another aspect of the present invention to provide a system and method of cleaning and/or disinfecting one or more dispensing lines between a take-off station and a dispensing station, which system and method reduce the chance of human error that can contribute to an unsafe cleaning.

It is another aspect of the present invention to provide a system and method of cleaning and/or disinfecting one or more dispensing lines between a take-off station and a dispensing station, which system and method eliminates or at least substantially reduces chemical exposure to humans.

It is another aspect of the present invention to provide a system and method of cleaning and/or disinfecting one or more dispensing lines between a take-off station and a dispensing station, which system and method minimizes the time in which the dispensing lines are off.

It is another aspect of the present invention to provide a system and method of cleaning and/or disinfecting one or more dispensing lines between a take-off station and a dispensing station, which system and method is reliable and repeatable.

It is another aspect of the present invention to provide a system and method of cleaning and/or disinfecting one or more draught beer dispensing lines between a keg coupler and a faucet.

These and other aspects are achieved by the present invention in that the automatic or semi-automatic Clean-In-Place system comprises

- an ozonated water valve inserted in the ozonated water conduit,
- a water valve inserted in the water conduit,
- a main conduit configured to in turns receiving water from the water conduit and ozonated water from the ozonated water conduit,
- the main conduit extends into a first plurality of n≥1 serially arranged flow distribution units,
- a flow distribution unit of the first plurality of flow distribution units comprises a second plurality of m≥2 serially arranged branch conduits on the main conduit,
- at least one of the at least two branch conduits has
  - at least one flow control valve disposed between a free branch end and its junction from the main conduit, and
  - a second coupler provided at the free branch end, which second coupler is adapted to couple in fluid communication with the first coupler,
- and
- an electronic control system configured to operate and control at least operative status of the ozonated water valve, the water valve and the flow control valves.

The automatic or semi-automatic Clean-In-Place system and method of the present invention utilizes ozone instead of caustic or acidic chemicals for cleaning the dispensing lines. Thus the only resources needed to operate the system are access to electric power and water. The waster products from the system and method are simply water and oxygen that can be discharged directly into the sewer. There is no need to use special collecting containers to collect waste.

The ozone is dissolved directly in flowing water. Ozonated water does not need chemical storage facilities and handling that might cause safety issue. The ozonated water does not constitute the toxic effects of ozone gas. Furthermore, by using ozonated water a post-rinsing step is not mandatory, although it might be preferred, because ozonated water does not leave any residual chemicals except water and oxygen. Thus no harmful by-products need to be handled or observed at the end of the cleaning process.

Ozonated water has instant antimicrobial properties and removes bio film, fungus, mold, yeast and beer stone. A further advantage is that water consumption for the cleaning is reduced. The cleaning water supply may serve for initially removal of debris, precipitates, and organic deposits from the dispensing line(s), where after the ozonated water serves to disinfect said dispensing line(s).

The second coupler is a convenient means to couple the flow distribution system to the dispensing line system to be cleaned and disinfected using ozonated water.

The automatic or semi-automatic Clean-In-Place system has one flow distribution unit or more serially arranged flow distribution units coupled to the dispensing line(s) connected to the dispensing station. In the context of the present invention the first plurality may be just n=1. The water valve and a selected number of flow control valves for opening and closing flow through the dispensing lines to be cleaned are then opened to flush said dispensing lines in a predetermined period. All or just some of the flow control valves can be cleaned in the same cleaning process. The operator may simply input his/her choice of flow control valves to be cleaned to the electronic control system. The operator may also input a certain user-set period of water cleaning, or the electronic control system of the automatic or semi-automatic Clean-In-Place system may be pre-programmed with a fixed water cleaning period.

After closing of the water valve the ozonated water valve is opened to subsequently flush the dispensing lines with ozonated water to conduct disinfection and kill microorganisms.

In the present embodiment the branch conduits of a flow distribution unit are arranged in series along the main conduit, and each branch unit has at least one flow control valve that can be operated individually via the electronic control system.

Within the context of the present invention the term “flow control valve” includes any kind of valve adapted to open and/or close a flow path at least partly in response to instructions from the electronic control system. The term “flow control valve” covers e.g. simple on/off valves and check valves, such as magnetic valves.

Preferably each of the branch conduits has a flow control valve.

In an alternative embodiment sub-branch conduits of a flow distribution unit can be arranged in parallel on a common branch conduit, and one or more flow control valves be used to operate all sub-branch conduits at the same time, and thus several dispensing lines at the same time.

The branch conduits and the sub-branch conduits may be operated individually, sequentially, and in selected arbitrary order.

In an alternative embodiment flow control valves of a flow distribution unit may be disposed upstream the junction between the main conduit and a branch conduit.

The electronic control system can be configured to in turns, and in any selected order and number of times, operate and control at least the ozonated water valve, the water valve and the flow control valves to convey water through the at least one dispensing line in a water cleaning period, of e.g. 5-10 minutes, to flush said dispensing line, and convey ozonated water to said at least one selected dispensing line in an ozonated water disinfection period, of e.g. 5-20 minutes, to disinfect said dispensing line(s).

The electronic control system may thus be configured to operate and control the cleaning process, such as the water cleaning period, the ozonated water disinfection period, the valves, the production of ozonated water, and which dispensing line(s) that is/are to be cleaned and disinfected. The automatic or semi-automatic Clean-In-Place system may include one or more flow sensors and/or pressure sensors at any appropriate positions along any of the conduits to monitor if the flow velocity is kept at a set value, and if the dispensers are open during flushing of the dispensing lines. The automatic or semi-automatic Clean-In-Place system may also monitor various kinds of electrodes measuring data of e.g. ozone concentration of the ozonated water, water temperature, and pH at any stage or position of the cleaning process. To monitor and control the various operational means and operational data the electronic control system is equipped with suitable computer means, including software and graphical user interface (GUI). The user may e.g. customize the cleaning via input to the GUI on a touch screen remote from the CIP-system.

The source of ozonated water can be any kind of electrolytic ozone generator or be ozone gas dissolved in water. The ozonated water produced by the electrolytic ozone generator can advantageously be produced on demand, e.g. by electrolysis of water from a water supply. Optionally the water supply for the electrolytic ozone generator is simply also the water supply for the cleaning water. It is however preferred that in case the ozonated water is produced by an electrolytic ozone generator, said water passes through a filter prior to entering the electrolytic cell(s). Preferably the cleaning water supply can be tap water.

If the number flow distribution units is n=1, and the number of branch conduits of a flow distribution unit is m=2, two dispensing lines can be cleaned at the same time. On the other hand the automatic or semi-automatic Clean-In-Place system of the present invention can be customized as to the current need by choosing the appropriate number n of flow distributions units in view of the number m of branch conduits of such a flow distribution unit. Said flow distribution units can be coupled in series to easily upscale the simultaneous cleaning and disinfecting capacity. The automatic or semi-automatic Clean-In-Place system of the present invention is thus a modular system to which further flow distributions units can be added in a very simple manner as times goes by and the need for cleaning and disinfecting more dispensing lines increases.

CIP systems having one flow distribution unit for each dispensing line are however also within the scope of the present invention.

An outlet end of the main conduct at the n'th of the serially arranged flow distribution units may be coupled in recycling fluid communication with the source of ozonated water via a recycle valve to avoid that ozonated water stays in the conduits and in other parts of the automatic or semi-automatic Clean-In-Place system when said system is out of use, and this way reduce risk of corrosive attack. The recycle valve may e.g. be closed when at least one of the flow control valves are open so that all ozonated water flows through the selected dispensing line(s). At the end of the cleaning and disinfection process all valves, including the flow control valve(s), the ozonated water valve and the water valve are to be closed before the first coupler and the second coupler are decoupled and the first coupler again is coupled to a take-off receptacle to establish flow of the content of the take-off receptacle through the dispensing line to the dispenser. Before said decoupling of said couplers the recycle valve may be opened by the electronic control system to empty the conduits of dissolved ozone.

In an advantageous embodiment a flow sensor may be provided in the main conduit, and/or in one or more of the branch conduits, and be operatively coupled to the electronic control system to ensure that in particular the flow of ozonated water is sufficient to deliver the appropriate amount of ozone required for the required level of disinfection.

In yet an advantageous embodiment a pressure sensor may be provided in e.g. the main conduit, and/or in the branch conduit(s), and be operatively coupled to the electronic control system to monitor and register if the dispensers are open, and are kept open, when water and ozonated water flow through the main conduit and the branch conduit (s). If the water pressure or ozonated water pressure is high, or suddenly becomes high, this is to be taken as an indication that one or more dispensers is/are closed, or has/have become closed, and maybe need(s) to be opened.

Commercial establishments, such as bars, restaurants and breweries, need to serve multiple beers on tap. They also need a place to store and chill their kegs in an area that is easily accessible so that kegs can be changed quickly. Keg beer is usually unpasteurized, so it has to stay cold to stay fresh, so typically the beer may pass through a cooling coil, and/or through a glycol cooling hose. Cooling usually keeps the beer at 1-2° C., which is important to keep the beer fresh and tasty. If the draught beer dispensing lines are not properly disinfected the tapped beer taste bad. A beer dispensing station typically has between 5 to 20 dispensing lines, in some cases just one or two dispensing lines, or up to 40 dispensing lines, or even more. The present invention can be customized to any arbitrary number of dispensing lines simply by adding additional flow distribution units.

Beer kegs are often placed in a cellar with 5-50 m long dispensing lines to the respective dispensers, the faucets, and when the beer keg lines are to be cleaned using conventional methods, the cleaner has to lift and move a lot of heavy stuff, including collecting, using and disposing harsh chemicals, at many different locations. It takes time, and is heavy unsafe work. The present invention only requires coupling the keg coupler to the second coupler, opening the faucets and starting the electronic control system to perform the cleaning and disinfection in the prescribed duration periods. No harsh chemicals are to be moved and disposed, in that the ozonated water goes directly to drain where it decomposes, and in that ozonated water can be produced on demand.

A drain manifold having a plurality of discharge hoses corresponding to the plurality of dispensing lines to be cleaned and disinfected may conveniently be part of the automatic or semi-automatic Clean-in-Place system of the present invention. A discharge hose of the drain manifold may be fitted to the dispenser during the cleaning and disinfecting method. The drain manifold may terminate into a common drain hose into which the discharge hoses discharge waste cleaning water and waste ozonated water.

During cleaning the dispensers may discharge directly into a drain, such as a sewer, sink, floor drain, or a discharge tray of the dispensing station, or a remote drain facility, e.g. by using the drain manifold and placing the common discharge hose in the drain.

Optionally each of the discharge hoses or the common drain hose may have a length enabling these hoses to at least extend into a drain tray of the dispensing station to discharge flushing cleaning water and disinfecting ozonated water towards a drain outlet of said drain tray without splashing. The discharge hoses or the common drain hose may preferably be transparent so that the liquid matter can be observed. Optionally the turbidity of the liquid flowing in the dispensing lines and the conduits can be monitored by means of a turbidity sensor, such as a turbidity meters adapted for fast analyzes of turbidity and for color monitoring. Monitor turbidity in beer, wastewater, biotech and chemical production applications is known to the skilled person. If the turbidity of the content in a liquid dispensing line turns out to be high this dispensing line may require longer cleaning period and/or longer disinfection period than other cleaning lines.

To prolong lifetime of the automatic or semi-automatic Clean-In-Place system it may be preferred that at least said conduits, said second coupler and said valves of the Clean-In-Place system are manufactured of ozone resistant material, preferably the ozone resistant material is selected from the group of materials comprising stainless steel 316, stainless steel 304, ceramics, polyvinyl chloride (PVC), polyethylene (PE), polycarbonate (PC), polytetrafluoroethylene PTFE, Teflon, silicone, and/or titanium. Preferably the dispenser, the dispensing lines and/or the first coupler can also be made from one of these materials.

The inventors of the present invention have established that the optimum concentration of dissolved ozone in the ozonated water for disinfection of draught beer dispensing lines is between at least 5 ppm, preferably at least 8 ppm, more preferred at least 10 ppm. 6 ppm may be preferred for most kinds of beer dispensing lines, however fruity or very sweet inhomogeneous or turbid beers types may require higher concentrations for cleaning and disinfecting the dispensing line.

The water cleaning period and the ozonated water disinfection period may be adjusted depending on the concentration of the ozone in the ozonated water, the pressure/velocity of the ozonated water and of the cleaning water, on the soiling of the dispensing line, frequency of cleaning and disinfection, and also the kind of matter normally flowing in the dispensing line(s). This list is not exhaustive and should not be construed as limiting when deciding the operational parameters for the cleaning and disinfection.

The ozone water disinfection period for disinfection of a draught beer dispensing lines may be e.g. be between 5 and 20 minutes, preferably between 5-15 minutes, and more preferred between 6-10 minutes, depending on the ozone concentration. At e.g. a ozone concentration of 6 ppm the draught beer dispensing lines may be flushed during about 15 minutes with ozonated water, and at mains water pressure of minimum 1 bar, typically about 2-4 bars, e.g. 8 liters per minute. But preferable a higher ozone concentration is used for a shorter period.

The electronic control system may include an operation module taking account of such parameters, e.g. based on measurements of status and condition of soiling of a dispensing line and/or data on the last cleaning and disinfecting operation, which have been logged by the electronic control system.

The present invention arose from a desire to provide a method and a system for maintenance of draught beer dispensing systems but is, as mentioned above, equally relevant for implementation with any kind of dispenser system that needs frequent cleaning off of deposits in the dispensing system components, including for removal of microorganisms and organic matter deposited in said system.

The automatic or semi-automatic Clean-in-Place system of the present invention is thus applicable for cleaning and/or disinfecting an infinity of various dispensing systems, including but not limited to dispensing systems for tapping other kinds of beverages, as well as dispensing systems for dispensing many different kinds of foodstuff, including but not limited to dispensing systems for dispensing foodstuff in the foodstuff industry, such as dispensing dairy products, dough in bakery lines, and any other kinds of food products, as well dispensing systems for dispensing drugs in the pharmaceutical industry, etc. This list is not exhaustive in that the automatic or semi-automatic Clean-In-Place system of the present invention can be used to clean and/or disinfect any imaginable system of dispensing line at small, medium or large scale, including at industrial level, due to the ability of being easy to upscale, including up-scaling as the need arises.

The automatic or semi-automatic Clean-In-Place system may comprise an electronic control switch adapted to verify that the first coupler and the second coupler are coupled fluid-tight together, thereby making the automatic or semi-automatic Clean-In-Place system safe, and keeping both the water valve and the ozonated water valve closed when said system it out of use.

The second coupler may in some embodiments have a spring-biased lid to protect its opening when the automatic or semi-automatic Clean-in-Place system is in the non-operative state. The spring inherently brings the lid to cover the opening into the second coupler, e.g. when said second coupler is not coupled to a first coupler. Thus the spring-biased lid prevents dripping of residual liquid from the flow distribution system when the automatic or semi-automatic Clean-in-Place system is not in use.

Since the distance between the storage of the take-off station and the dispensing station may be rather long at some places the electronic control system may be configured to be operated over a wireless network.

The water supply for providing filtered water to the electrolytic ozone generator may, as mentioned before be tap water. It may however be preferred that said filtered tap water is warm, e.g. having a temperature of between 20° C. and 25° C., at which temperature the production of ozone is very efficient. The filtered water can however have any convenient temperature, including being cold.

Also the cleaning water may be warm to initially dissolve and/or disintegrate larger deposits, such as organic deposits, in the dispensing lines.

The present invention also concerns a method of cleaning a system of dispensing lines between a take-off station and a dispensing station by means of the automatic or semi-automatic Clean-In-Place system described above.

The method comprises providing the automatic or semi-automatic Clean-In-Place system according to any of the preceding claims, and performing the steps of a) disconnecting the selected one or more first couplers at the end of the respective dispensing lines from their respective take-off receptacle, b) coupling a second coupler(s) to each of the free first coupler (s), c) opening the dispensers associated with the respective dispensing line, d) operating the electronic control system to operate the ozonated water valve, the water valve and the flow control valves to conduct a disinfection cycle including:

d1) opening a selected number of flow control valves, d2) opening the water valve and flushing the associated dispensing line(s) between the first coupler and a discharge opening of the dispenser associated with the dispensing line with water in a water cleaning period, d3) closing the water valve, d4) opening the ozonated water valve and disinfecting, in an ozonated water disinfection period, the dispensing line between the first coupler and the discharge opening of the dispenser with ozonated water produced by an electrolytic ozone generator, d5) closing the ozonated water valve, d6) optionally repeating steps d2) and d3); or optionally repeating steps d2) to d5), e) closing the flow control valves, and f) optionally disconnecting the first coupler and the second coupler.

It should be emphasized that not all dispensing lines need to be cleaned and/or disinfected at the same time. A number of dispensing lines can be treated and completed at the time. Yet an option is to partly treat some of the dispensing lines with either water or ozonated water.

In an exemplary embodiment step d1) is performed on all flow control valves and the dispensing lines subjected to step d2). Then step d4) is performed on one or more dispensing lines, optionally all dispensing lines. How many of the dispensing lines that are to be subjected to step d4) may be a user input made by the operator. In step d5) the ozonated water valve may be closed already once a dispensing line has been filled with ozonated water to allow the intake volume of ozonated water to react inside the dispensing line. In such an embodiment step d2) is repeated.

The dwell time of in-taked ozonated water inside the dispensing lines saves production costs and requires only a minimum of ozonated water.

In an alternative embodiment the ozonated water may also serve to simultaneously flush a dispensing line during the reaction period, whereby time for subsequent flushing out waste decomposition products by means of cleaning water, as in step d2) can be reduced substantially.

Step d4) performed on a first selected dispensing line may e.g. have a dwell time, thus a disinfection period of 2 min. while another may dispensing line is flushed for 2 min. Then step d2) is repeated, e.g. for 90 sec. for the first dispensing line and the other for 45 sec.

The electronic control system facilitates a multiplicity of combinations of the above. E.g. to flush some of the dispensing lines with ozonated water and allow other dispensing lines to be subjected to ozonated water in a dwell time is also foreseen by the management of the electronic control system.

Thus by operating the flow control valves on the respective branch conduits in any desired order, regime and on demand, the Clean-In-Place system and method of its use offers a multiplicity of options to the user that hitherto not has been available and thereby saving time, costs and being substantially more user-friendly than know so far by the conventional systems and methods for the same purpose.

A cleaned disinfected dispensing environment can be re-established by conducting the steps of:

g) coupling the first coupler to the take-off receptacle to establish fluid communication to the open dispensers, h) allowing a content of the take-off receptacle to flush the dispensing line between the first coupler and the discharge opening in a final flushing period, and i) closing the dispensers.

The method may further comprise step b1) between step b) and c), wherein step b1) comprises coupling a drain hose to a discharge opening of a dispenser, and step j), which is performed after step i), wherein step j) comprises decoupling the drain hose of the discharge opening of the dispenser to place said dispenser(s) in a ready-to-dispense condition, such as a draught condition.

The method may further comprise an additional step of recycling residual produced ozonated water to any of the ozonated water source, the ozonated water supply or a drain facility at the latest after step e).

The method may further comprise one or more of in step d) adjusting the temperature of water supplied to the electrolytic ozone generator to between 20° C.-25° C. during electrolysis, and cooling the produced ozonated water using a cooling facility of the at least one dispensing line.

The invention further relates to a draught beer system comprising the above described automatic or semi-automatic Clean-In-Place system wherein the take-off receptacle is a keg, optionally a beer keg, the dispensing station is a dispensing tower, the dispenser is a draught beer faucet, and the first coupler is a keg coupler.

Figure 2:
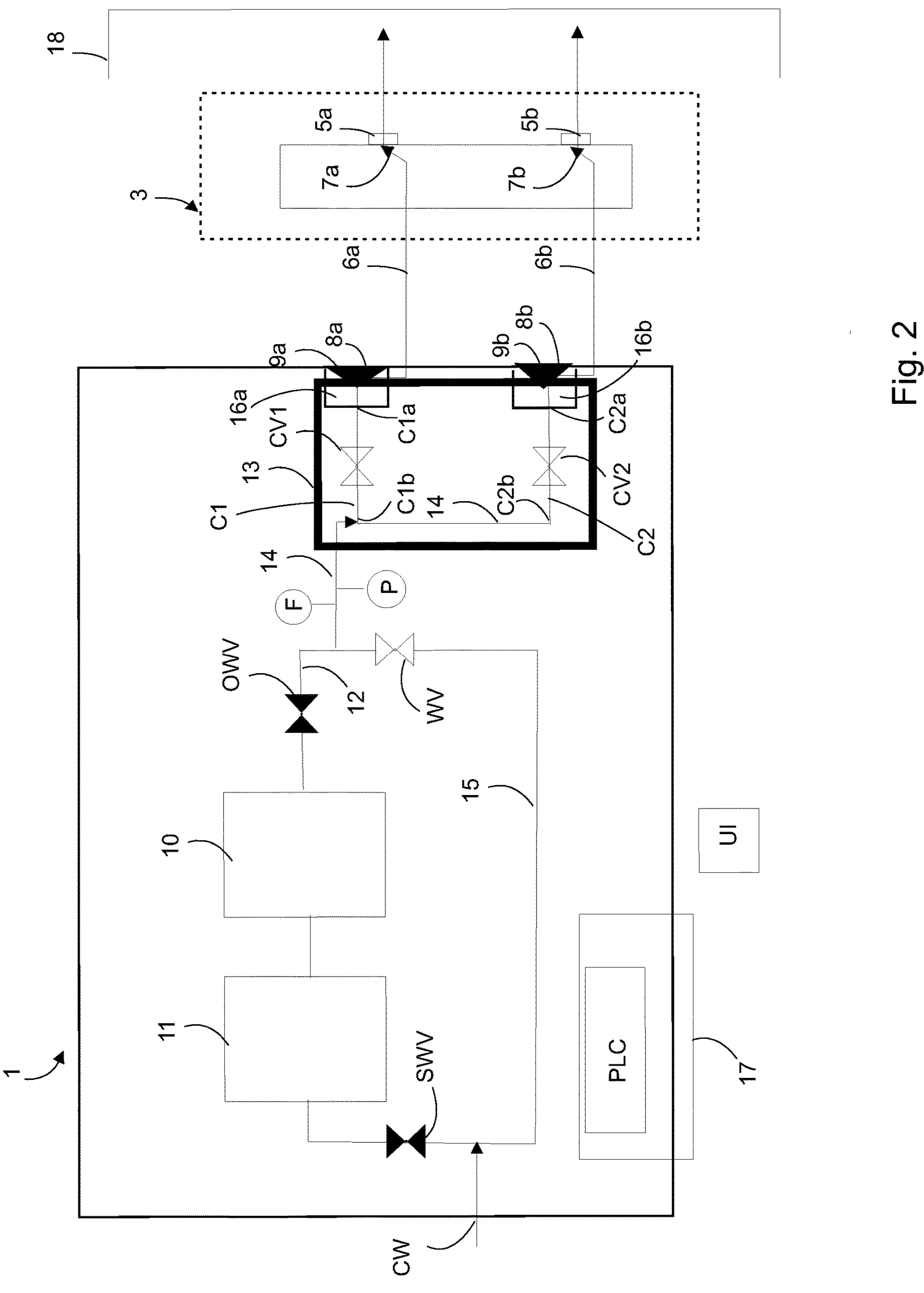
Figure 3:
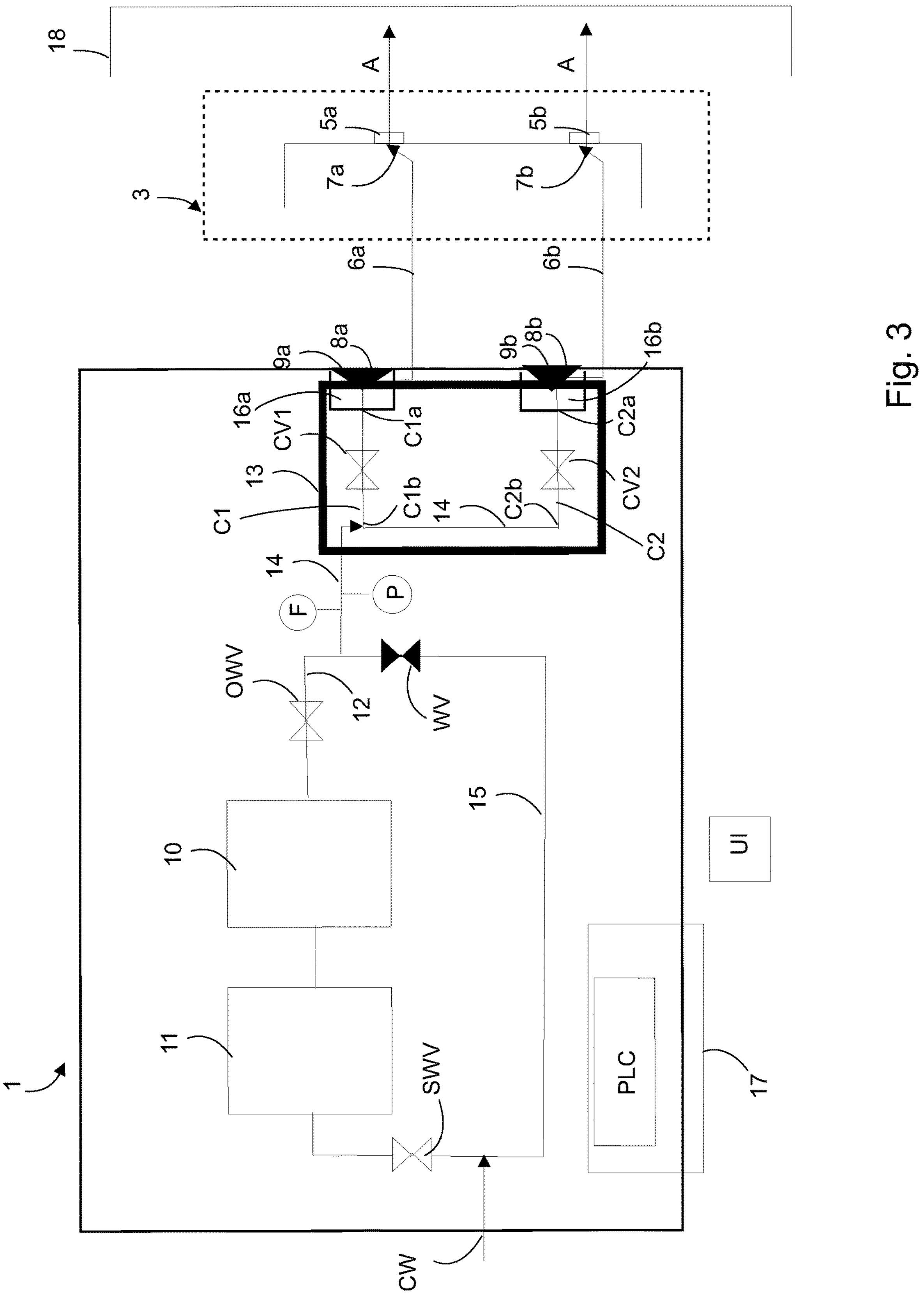
Figure 4:
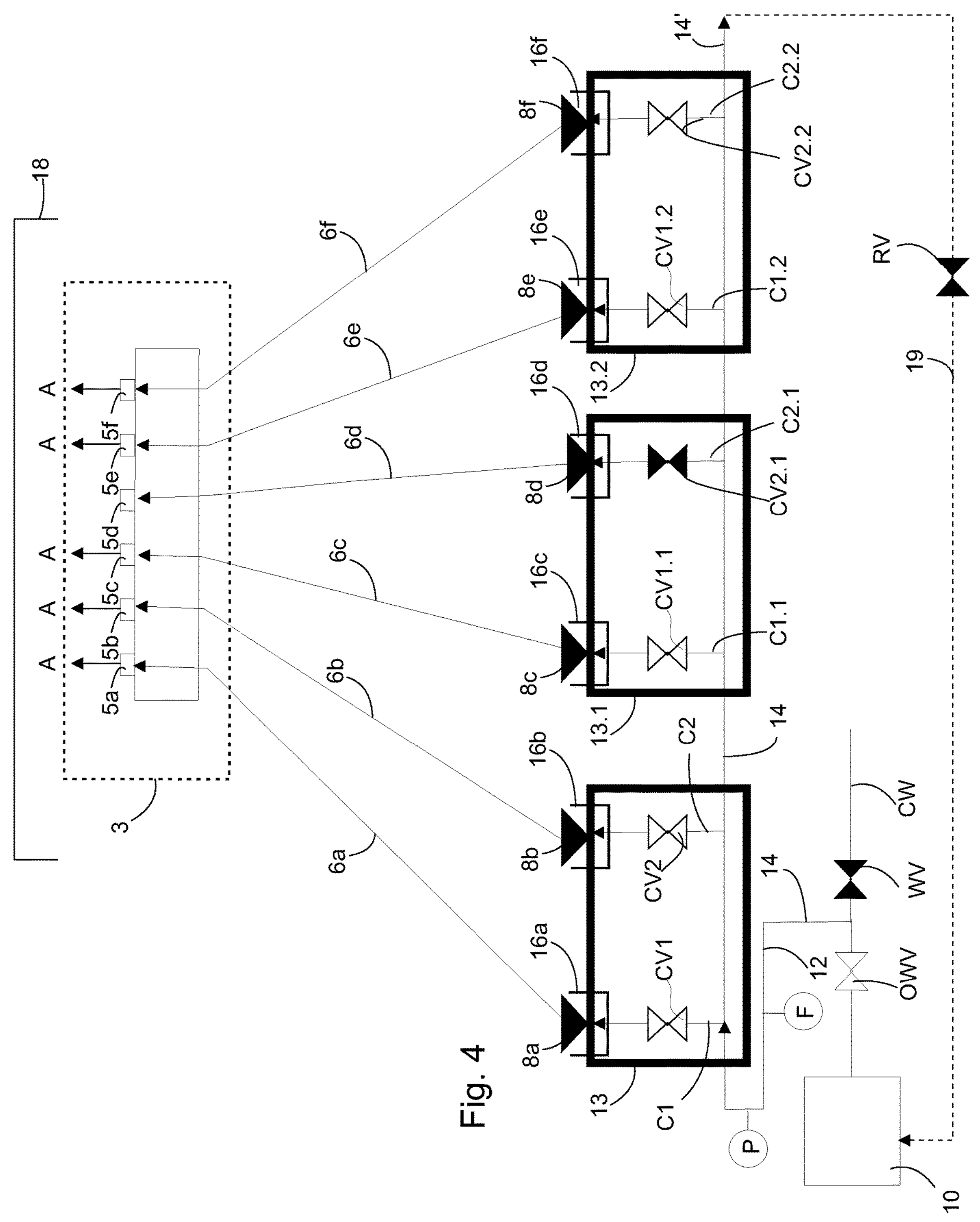
Figure 5:
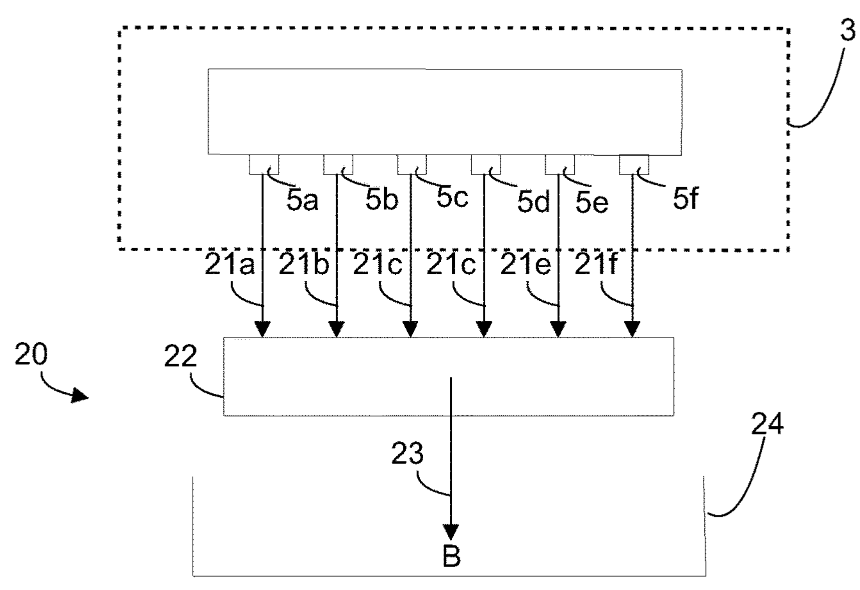
Figure 10:
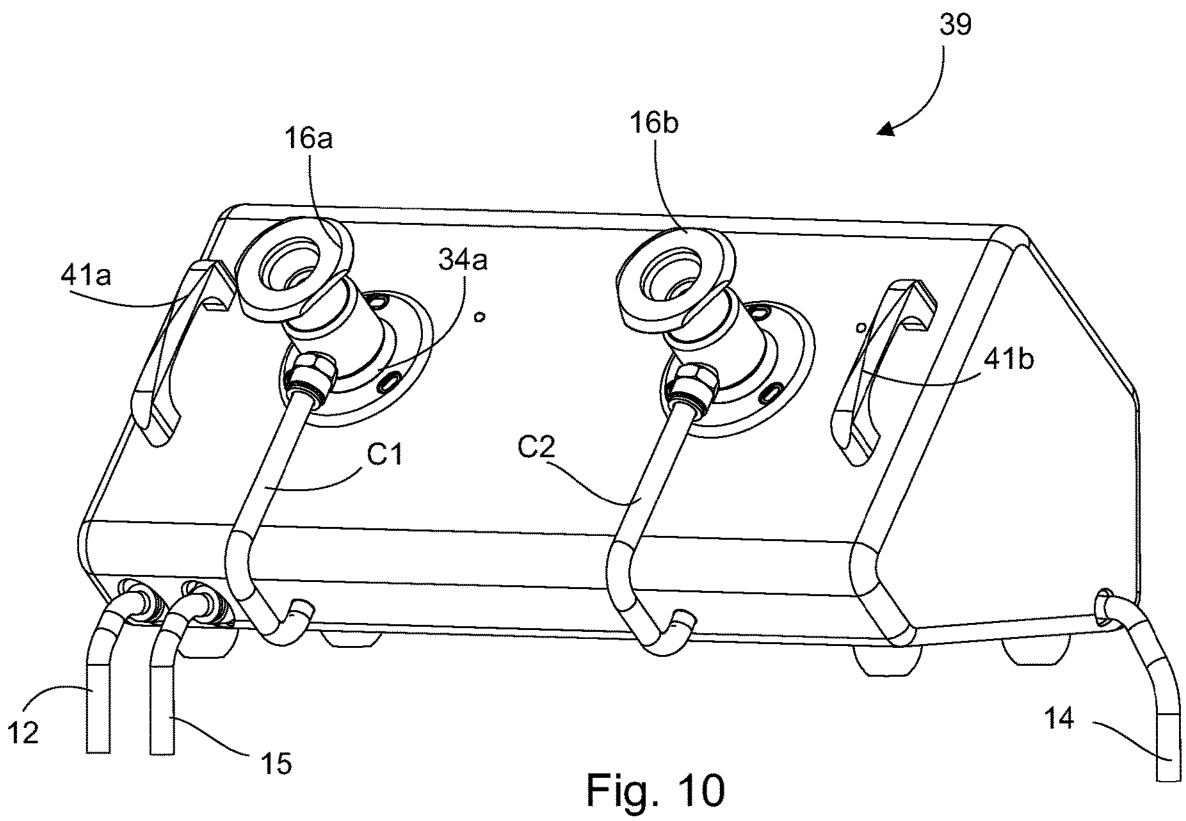
Figure 6:
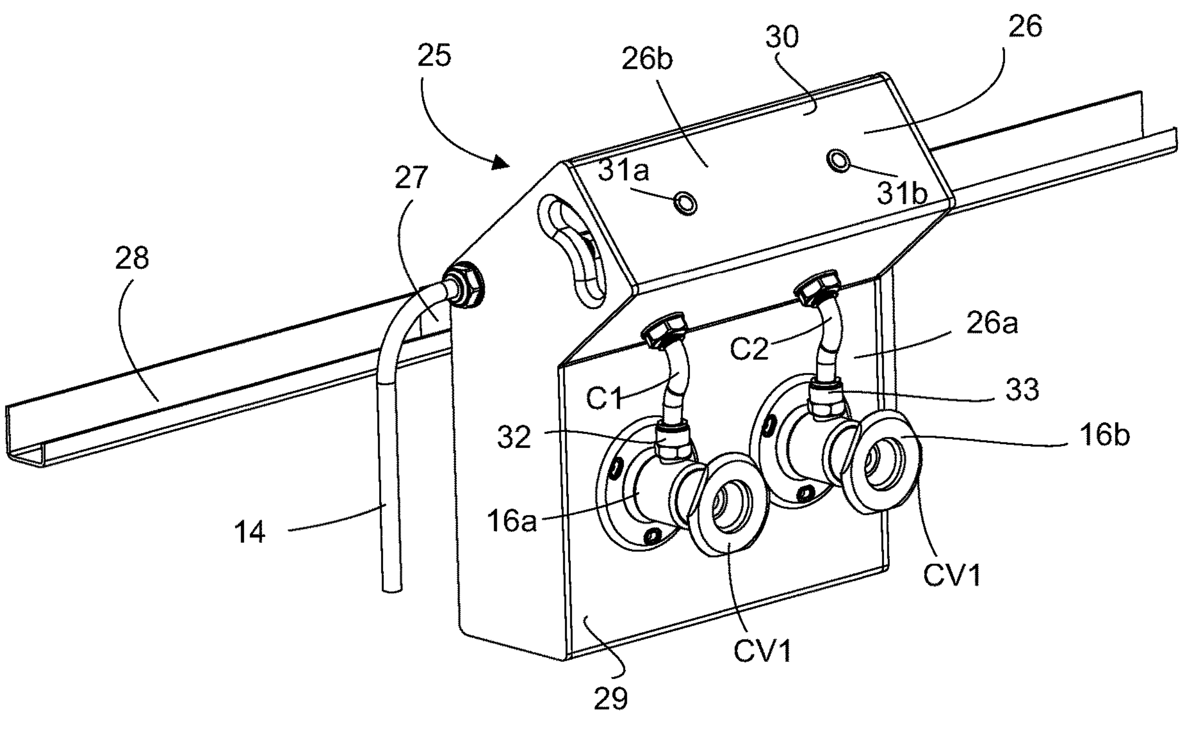
Figure 7:
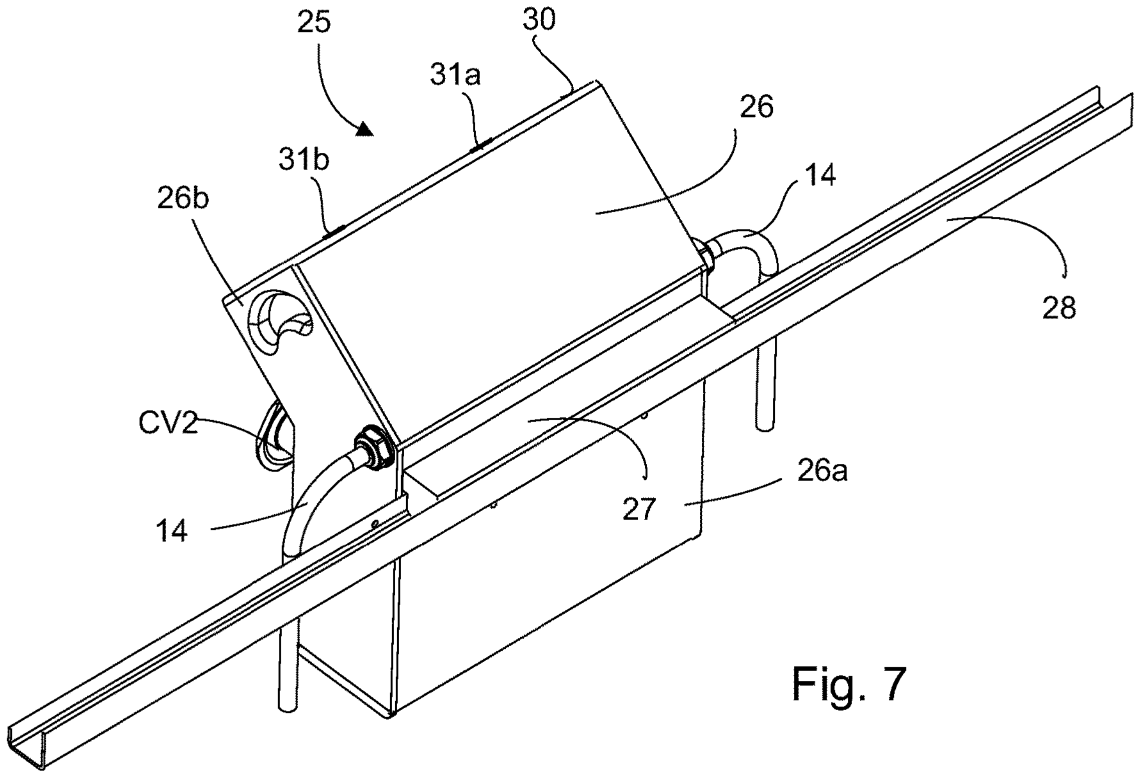
Figure 8:
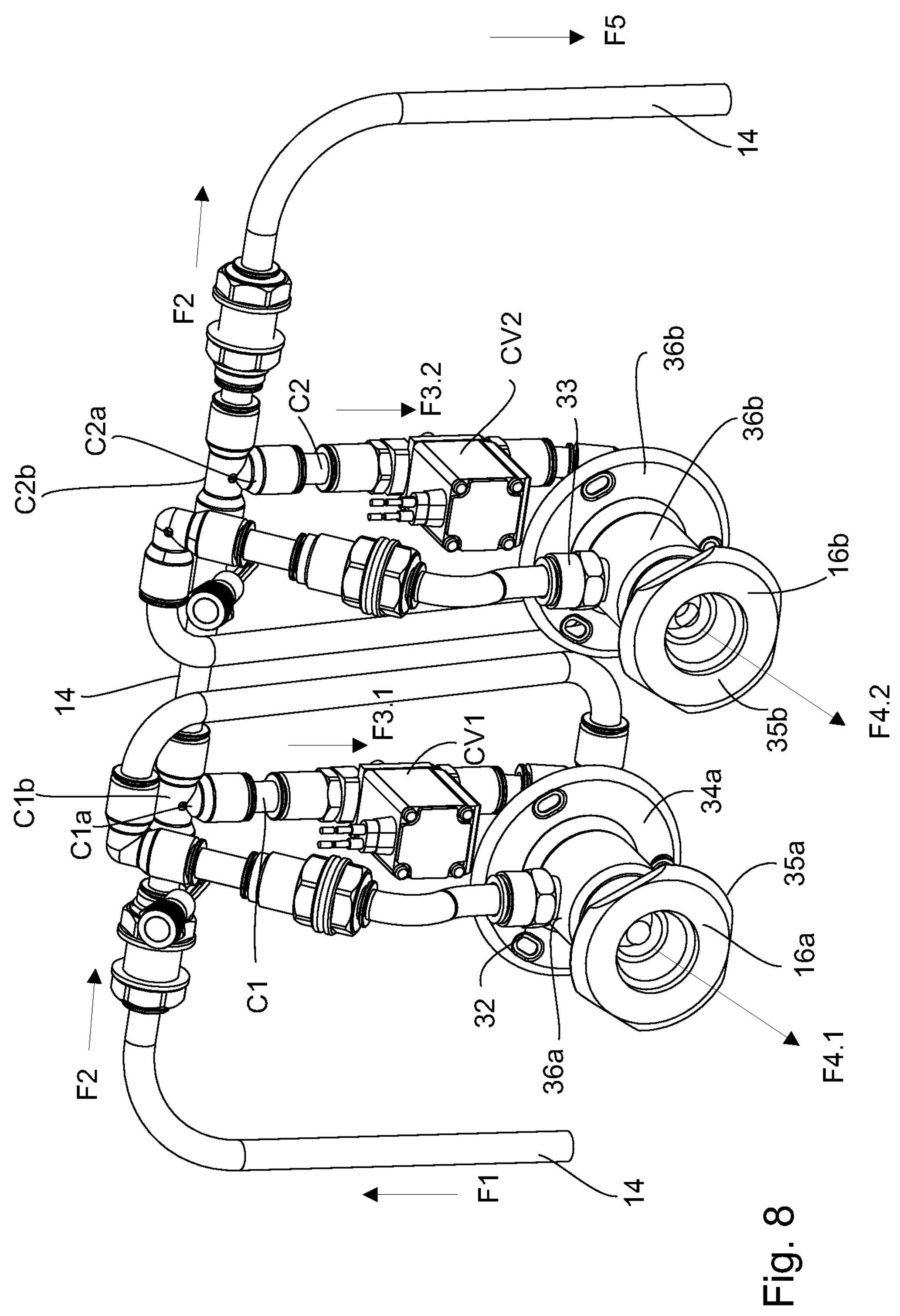
Figure 9:
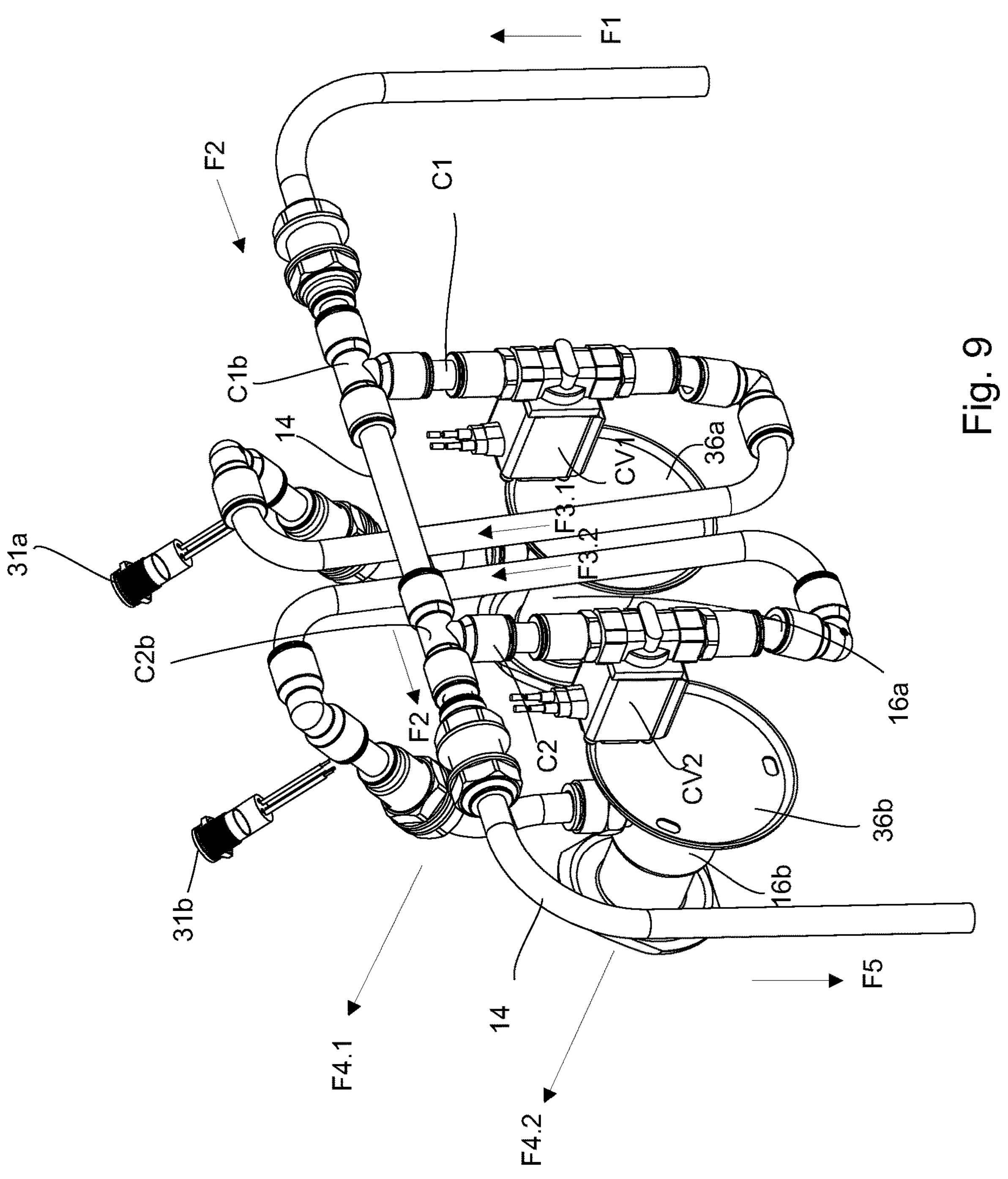
Figure 11:
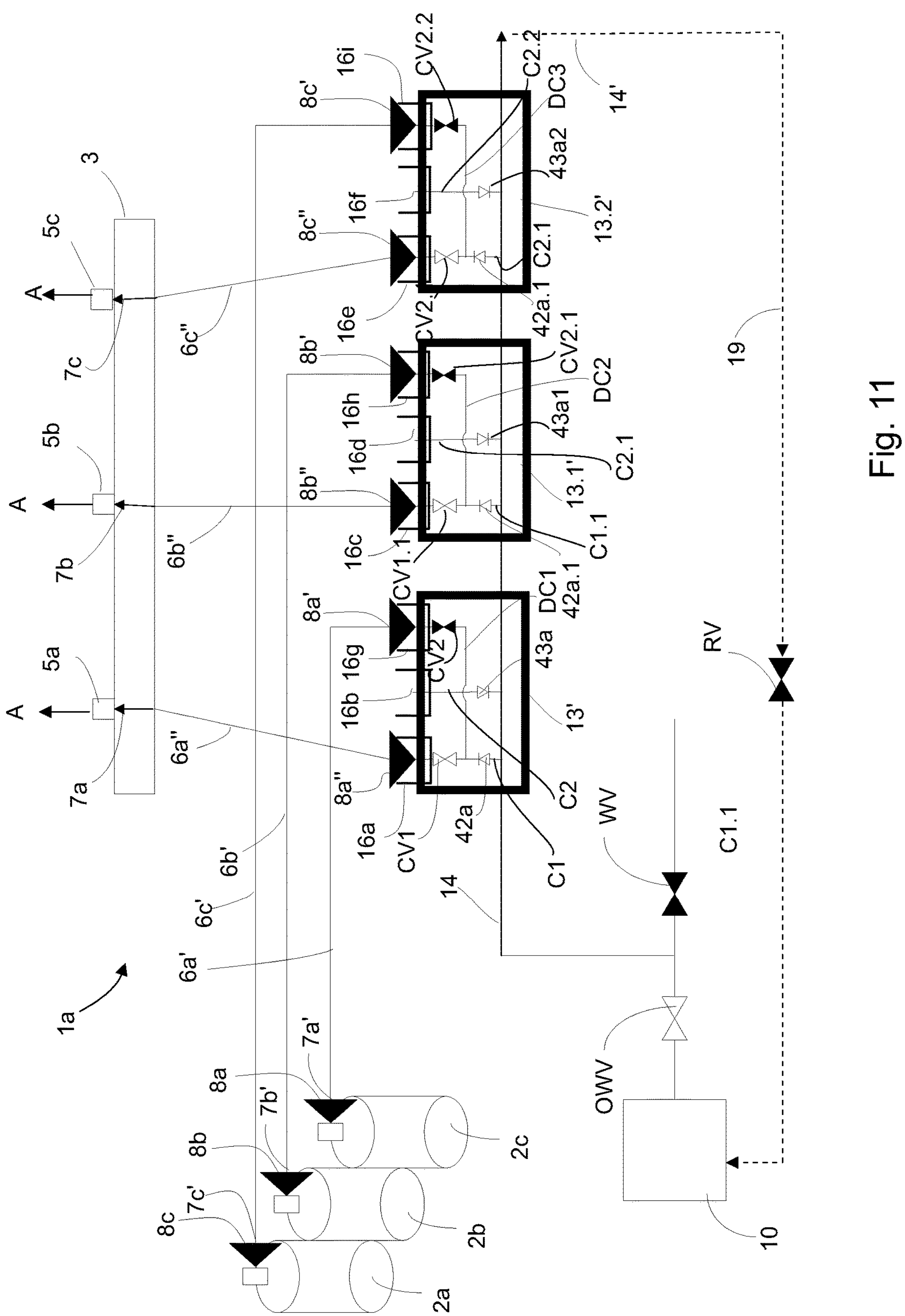
Figure 12:
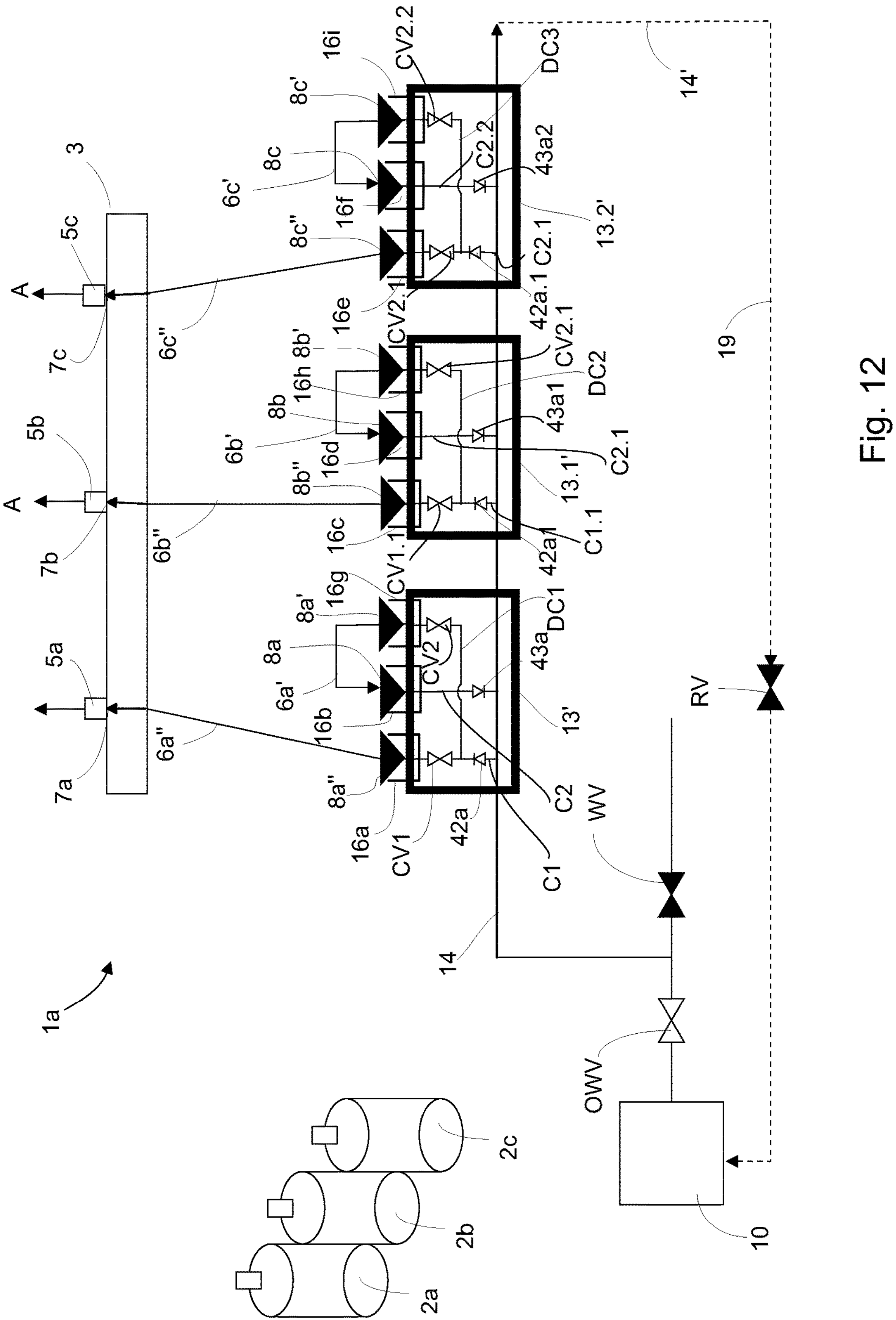
Figure 13:
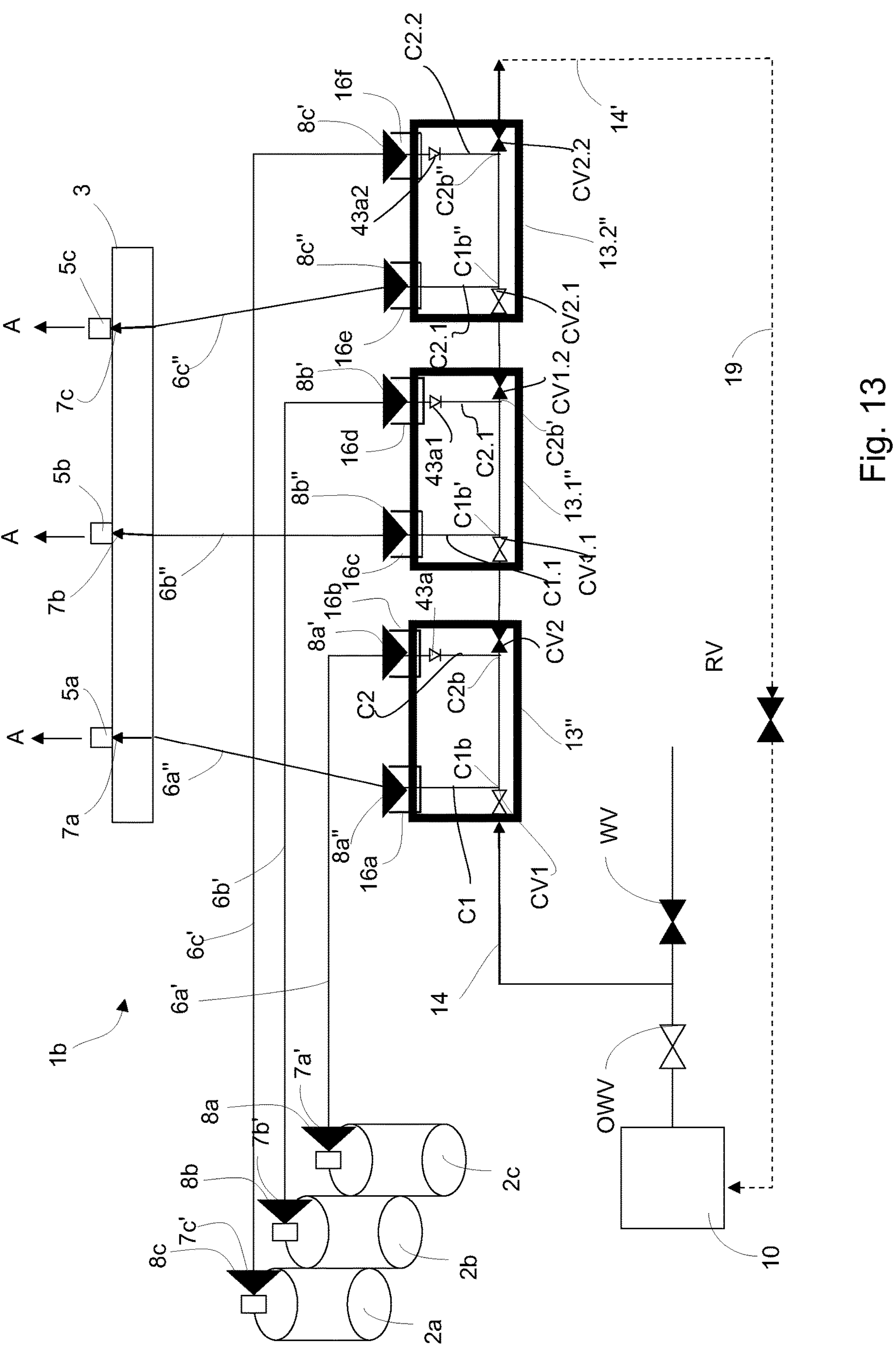

The automatic or semi-automatic Clean-In-Place system and its method of use will be described in more details with references to the accompanying drawing, in which FIG. 1 is a schematic overview of an embodiment of an automatic or semi-automatic Clean-In-Place system shown together with a schematic view of a take-off station coupled to a dispensing station, FIG. 2 is a schematic overview of a first embodiment of an automatic or semi-automatic Clean-In-Place system seen in FIG. 1 with a first embodiment of a flow distribution unit coupled to the dispensing lines of a dispensing station in a water cleaning step, FIG. 3 shows the same in an ozonated water disinfecting step, FIG. 4 is a principle sketch showing three serially connected flow distribution units of the first embodiment coupled to a common dispensing station in an ozonated water disinfecting step, FIG. 5 is a principle sketch of discharging cleaning water and ozonated water from the common dispensing station seen in FIG. 4 to a common drain facility, FIG. 6 is a perspective front view of design of the first embodiment of a flow distribution unit configured for being suspended on a surface, such as a wall, FIG. 7 shows the same seen from the rear side, FIG. 8 is a perspective front view of said first embodiment of a flow distribution unit without the housing, FIG. 9 shows the same from the rear side, FIG. 10 is a perspective front view of a second embodiment of a flow distribution unit configured for being placed on a surface, such as a table top, FIG. 11 is a schematic overview of a second embodiment of an automatic Clean-In-Place system, in a mode in which the first coupler remains on the take-off station during the cleaning and/or disinfection process, FIG. 12 is a schematic overview of the same utilized to clean and/or disinfected only a part of the length of full dispensing lines between take-off station and dispensing station, and FIG. 13 is a schematic overview of a third embodiment of an automatic Clean-In-Place system, in a mode in which the first coupler remains on the take-off station during the cleaning and/or disinfection process.

In the below detailed description the automatic or semi-automatic Clean-In-Place system is for simplicity named "CIP-system", and purely as an example, the CIP-system is described for use in cleaning and disinfecting a draught beer dispensing system.

The dispensing towers of the draught beer dispensing system shown in the figures have two, three or six faucets, and the flow distribution unit is shown to have two or three second couplers. Thus one flow distribution unit of the CIP-system can clean more than one dispensing lines at the same time. Emphasis is made that any number of faucets of a dispensing system is within the scope of the present invention as more and more flow distribution units can be placed in a consecutive series. The flow distribution unit may have any appropriate number m of branch conduits, and flow distribution units with different m-values can be connected in series.

In the figures a black flow control valve indicates that said valve is closed. A white valve indicates that said flow control valve is open.

Although not shown in the drawing it is to be understood that electrics and electronic components are connected to a power source, as well as the CIP-system may have a back-up power source, such as a battery to deliver emergency power.

The term "conduit" includes hoses, tubes and pipes. This list is however not exhaustive.

FIG. 1 is a schematic overview of a CIP-system 1 shown together with a schematic view of a take-off station 2 coupled to a dispensing station 3. The dispensing station is a draught beer dispensing tower 4 having two faucets 5*a*,5*b*. A dispensing line 6*a*,6*b* has a dispenser end 7*a*,7*b* coupled to the faucets 5*a*,5*b* opposite the take-off ends 7*a*',7*b*', which are coupled to a first coupler 8*a*,8*b* in form of a keg coupler 9*a*, 9*b*. In the situation shown in FIG. 1 the keg couplers 9*a*,9*b* are de-coupled the respective kegs (not shown) and are ready for being coupled to the CIP-system 1 to clean and disinfect the dispensing lines 6*a*,6*b*, as respectively shown in FIG. 2 that shows step d2) and in FIG. 3 that shows step d4).

The CIP-system 1 has a source of ozonated water 10, e.g. an electrolytic ozone generator that receives filtered water via filter unit 11 from a source of cleaning water, e.g. tap water, when supply water valve SWV is open, as seen in FIG. 3. produced ozonated water can flow into ozonated water conduit 12 through ozonated water valve OWV to enter a flow distribution unit 13 via main conduit 14. In FIGS. 1-3 n=1 and m=2.

When supply water valve SWV is closed, as seen in FIG. 2, cleaning water can flow into water conduit 15 through a water valve WV inserted in said water conduit 15 to enter the main conduit 14 to proceed into the first embodiment of a flow distribution unit 13.

The flow distribution unit 13 has two branch conduits C1,C2 arranged in series, which branch conduits C1,C2 branch from the main conduit 14 inside flow distribution unit 13. Each branch conduit C1,C2 has a flow control valve CV1,CV2 disposed between a free branch end C1*a*,C2*a* and its junction C1*b*,C2*b* from the main conduit 14. Each free branch end C1*a*,C2*a* has a respective second coupler 16*a*, 16*b*, a so-called cleaning adapter, which second coupler 16*a*,16*b* is adapted to couple in fluid communication with the first coupler 8*a*,8*b*, thus with the keg coupler 9*a*,9*b*, as shown in FIGS. 2 and 3, of the dispensing station 3, to also clean and disinfect said keg couplers 9*a*,9*b* in the same steps as when cleaning the entire dispensing lines 6*a*,6*b*. Cleaning water or ozonated water pass through the dispensing lines 6*a*,6*b* and into the faucets 5*a*,5*b* to be discharged into a drain 18.

An electronic control system 17 comprises a suitable programmed control means, e.g. a PLC provided with a suitable PLC program, or other kind of computer or computational means, including means such as suitable software programs that runs on a computer, and is developed and customized for operating and controlling the CIP-system. Controlling the CIP-system 1 comprises at least controlling opening and closing of the ozonated water valve OWV, the water valve WV and the flow control valves C1,C2, optionally also controlling the cleaning water valve and the supply water valve, the ozonated water disinfection period T1, and the water cleaning period T2. Via a user interface UI, such as a handheld device, the operator can customize the cleaning process to set the aforementioned periods T1,T2, and open and close e.g. the flow control valves C1,C2 in case just some dispensing lines 6*a*,6*b* are to be cleaned. Electronic communication to the CIP-system 1 may be achieved using a user interface UI, such as a graphical user interface GUI, over a wireless network, such as using WI-FI, to allow the operator to input operative data to the CIP-system from a remote location, thereby saving valuable maintenance time.

A flow sensor F and a pressure sensor P is inserted in the main conduit 14 to monitor the flow velocity and pressure, respectively, of cleaning water and ozonated water through the flow path comprised of the main conduit 14, the second couplers 16*a*,16*b*, the first couplers, 8*a*,8*b*, the dispensing lines 6*a*,6*b*, and the faucets 5*a*,5*b*. If the flow velocity is too high or too low, thus outside a predefined interval, the ozonated water disinfection period T1 may be too short or take too much time. If the pressure is too high it could be an indication that one or more faucets have not been opened so that cleaning water and ozonated water cannot discharge to pass freely into the common drain 18, as indicated by arrows A. More sensors and different sensors can be provided anywhere in one or more of the conduits of the CIP-system 1, and just of the flow sensor F and the pressure sensor P may be needed. If the mains pressure turns out to be unsatisfactory to conduct the method of the present invention the CIP-system may include one or more pumps arranged in relevant conduits.

In the set-up shown in FIG. 4 n=3 flow distribution units 13, 13.1, 13.2 are arranged in series to serve a maximum total of six faucets 5*a*,5*b*,5*c*,5*d*,5*e*,5*f* of a dispensing station 3. Accordingly the total number of branch conduits C1,C2; C1.1,C2.2; C1.2,C2.2 is m=6. The second couplers 16*a*,16*b*, 16*c*,16*d*,16*e*,16*f* at the ends of the branch conduits C1,C2; C1.1,C2.2; C1.2,C2.2 are coupled to the second couplers 8*a*,8*b*,8*c*,8*d*,8*e*,8*f*, of the dispensing lines 6*a*,6*b*,6*c*,6*d*,6*e*,6*f* which oppositely are connected to the faucets 5*a*,5*b*,5*c*,5*d*, 5*e*,5*f*. Thus the CIP-system seen in FIG. 4 is a modular build-up system comprising several flow distributions units 13 utilizing the same cleaning water source and the same ozonated water source. It should be emphasized that the CIP-system can be up-scaled to any desired scale and need.

At the last flow distribution unit 13.2. of the series of flow distribution units 13; 13.1; 13.2 the main conduit 14 may, via recycle conduit 19, recycle its residual content of ozonated water at the end of step d4) to the source of ozonated water 10, or to the ozonated water conduit 15, after the flow control valves CV1; CV1.1; CV1.2 have been closed. In the present case residual content of ozonated water is recycled to the electrolytic ozone generator 10, so that said flow distribution units 13,13.1,13.2 and corresponding branch conduits 14,C1,C2,C1.1,C2.1,C1.2,C2.2 are substantially emptied of ozonated water, thereby reducing exposure time of said flow distribution units 13; 13.1; 13.2 to ozonated water, and prolonging lifetime of their structural components. Recycle conduit 19 has a recycle valve RV that is closed until the cleaning method has been completed, e.g. when the electronic control system registers that the flow control valves CV1; CV1.1; CV1.2 have been closed, or registers that the first couplers 8*a*,8*b* and the second couplers 16*a*,16*b* have been disconnected. In the exemplary schematic sketch seen in FIG. 4 the flow control valve CV2.1 of the flow distribution 13.1 in the middle is closed, and the faucet 5*d*, dispensing line 6*d*, and the first coupler 8*d* are not being cleaned or disinfected. Thus FIG. 4 illustrates the option of customizing which dispensing line(s) to be cleaned.

FIG. 5 is a principle sketch of a drain manifold 20 having a plurality of m=6 discharge hoses 21*a*,21*b*,21*c*,21*d*,21*e*,21*f* secured to the outlets of the m=6 faucets 5*a*,5*b*,5*c*,5*d*,5*e*,5*f*. The discharge hoses 21*a*,21*b*,21*c*,21*d*,21*e*,21*f* discharge via a manifold body 22 into a common drain hose 23 that may have any suitable convenient length to reach a selected drain facility 24, as indicated by arrow B.

FIGS. 6 and 7 show a wall-suspended flow distribution unit, in the following called a wall-board 25. In FIG. 6 the wall board 25 is seen from the front with exposed second couplers 16*a*,16*b*. In FIG. 7 the same wall board 25 is seen from the rear side.

The wall board 25 has a housing 26 that accommodates the arrangement of the main conduit 14, the branch conduits C1,C2 and the flow control valves CV1,CV2, as seen in more details in the fragmentary views of FIGS. 8, 9 and 10.

The housing 26 has a rear suspension means 27 that is adapted to engage a wall-mounted coupling rail 28. The wall-board 25 can thus easily be suspended hanging on a wall. The wall-board 25 can be placed in a fixed position, such as screwed to the coupling rail 28, or be free to slide along the coupling rail 28. The housing 26 has a lower housing part 26*a* with a lower front wall 29 to which the second couplers 16*a*,16*b* are mounted protrudingly. The second couplers 16*a*,16*b* protrude from the lower front wall 29 and define a flow path to the branch conduits C1,C2, which branch conduits C1,C2 are externalized from an upper housing part 26*b* of the housing 26. The lower housing part 26*a* provides a solid support for the second couplers 16*a*,16*b* when said second couplers 16*a*,16*b* are to couple and de-couple the second couplers 8*a*,8*b*, such as the keg couplers 9*a*,9*b*. The lower housing part 26*a* extends upwards into the upper housing part 26*b*, which upper housing part 26*b* bends away from the wall, on which the housing hangs, by an angle of ≤90° to turn a front face 30 of the upper housing part 26*b* for easy visual inspection, e.g. inspecting and monitoring indicators 31*a*,31*b* provided at the front face 30 of the upper housing part 26*b* to visually identify whether a dispensing line 6*a*,6*b* is open or not during performing the cleaning and disinfection process. The angle between the upper housing part 26*b* and the lower housing part 26*a*, when seen from the front of the housing, is ≥90°. Suitable indicators 31*a*,31*b* can e.g. be RGB LEDs operated by the electronic control system.

As seen in FIG. 8 the water or ozonated water flows via the main conduit 14, as indicated by arrow F1, and enters the wall board 13 at the top of upper housing part 26*b* of the housing 26, as indicated by arrow F2. At a first junction C1*a* the main conduit 14 has a first branch conduit C1, as indicated by arrow F3.1, and at a subsequent downstream second junction C2*a* the main conduit 14 has a second branch conduit C2, as indicated by arrow F3.2, whereafter the main conduit 14 exits the wall board 25 as indicated by arrow F5, optionally extends into recycle conduit 19 or another wall board.

The first branch conduit C1 and the second branch conduit C2 have a respective inline flow control valve CV1,CV2 downstream the respective junction C1*a*,C1*b*. Said first branch conduit C1 and said second branch conduit C2 then turn a couple of times until they enter the second couplers 16*a*,16*b*, thus the cleaning adapters. The turning of the branch conduits C1,C2 allows a compact arrangement of the flow path inside the housing 26, and thus provides a very compact wall board 25 that does not take up much space when suspended on the wall (not shown).

The free branch end C1*a* of the first branch conduit C1 is secured to a first inlet 32 of the second coupler 16*a*, and the free branch end C2*a* of the second branch conduit C2 is secured to a second inlet 33 of the next second coupler 16*b* thereby arranging said second couplers 16*a*,16*b* in series along the main conduit 14. Cleaning water or ozonated water can then flow out of the second couplers 16*a*,16*b*, as indicated by arrows F4.1,F4.2, when the first couplers 8*a*,8*b*, e.g. the keg couplers 9*a*,9*b*, are coupled thereto, as seen in FIGS. 2 and 3.

The second couplers 16*a*,16*b* each have a respective rear mounting flange 34*a*,34*b*, a free front flange 35*a*,35*b* and a tubular flow body 36*a*,36*b* in-between said flanges 35*a*,35*b*; 36*a*,36*b*. The free front flange 35*a*,35*b* has a respective inlet opening 37*a*,37*b* to a cleaning channel 38*a*,38*b* in fluid communication with the inlets 32,33. The rear mounting flange 34*a*,34*b* are the part of the second couplers 16*a*,16*b* utilized to secure the second couplers 16*a*,16*b* to the housing 26, and the free front flange 35*a*,35*b* is adapted for coupling with the first couplers 8*a*,8*b*.

FIG. 10 shows a bench model of a flow distribution unit 39, in which the ozonated water valve OWV and the water valve WV are hidden inside the housing 40. The ozonated water conduit 12 and the cleaning water conduit 15 also merge into the main conduit 14 inside the housing 40. The functional principle otherwise corresponds to that of the wall board 25. The handles 41*a*,41*b* make it easy to move the distribution unit 39 around, so that hoses and conduits of the CIP-system can be shortened because the CIP-system can be brought to the dispensing lines.

The front flanges 35*a*,35*b* may conveniently have a universal design configured to couple with any desired second coupler 8*a*,8*b*, e.g. a keg coupler 9*a*,9*b*.

However in case the keg coupler design changes the second couplers can easily be demounted the housing and replaced with another appropriate second coupler that fits to engage this new design of a keg coupler. In the alternative an intermediate coupling component may be used as a transition member between the existing second coupler and the new design of a first coupler. The CIP-system of the present invention may include several intermediate replacement coupling components to mate with any imaginable design of first couplers thereby making the CIP-system of the present invention multifunctional and independent of a specific first coupler design.

The flow path F1,F2,F3.1,F3.2,F41,F4.2,F5 is assembled of appropriate lengths of hoses, pipes and/or other kinds of conduits assembled by means of tight fittings. Such fittings are known to the skilled person and will not be discussed in further details.

FIG. 11 is a schematic overview of a second embodiment of a Clean-In-Place (CIP) system 1*a* in accordance with the present invention. The second embodiment of a CIP-system 1*a* is a modification of the first embodiment of an automatic and/or semi-automatic Clean-In-Place system 1, and for like parts same reference numerals are used.

The second embodiment of a Clean-In-Place (CIP) system 1*a* has n=3 modified flow distribution units 13',13.1',13.2', each operating on one dispensing line 6*a*',6*a*"; 6'*b*,6*b*"; 6*c*',6*c*" and the associated dispenser 5*a*,5*b*,5*c*. The modified flow distribution unit 13',13.1',13.2' constitutes a second embodiment of flow distribution unit according to the present invention.

The CIP-system 1*a* is highly automatic in that the first couplers 8*a*,8*b*,8*c* at the respective take-off ends 7*a*',7*b*',7*c*' of the dispensing lines 6a',6a"; 6'b,6b"; 6c',6c" can remain on the respective take-off receptacles 2a,2b,2c during the cleaning and/or disinfection process.

The modified flow distribution unit 13',13.1',13.2' has n=2 branch conduits C1,C2; C1.1,C2.1; C1.2,C2.2 on the main conduit 14, a first branch conduit C1,C1.1,C1.2 and a second branch conduit C2,C2.1,C2.2 in series with the first branch conduit C1,C1.1,C1.2. The first branch conduit C1,C1.1, C1.2 has a first check valve 42a,42a1,42a2 followed by a first flow control valve CV1,CV1.1,CV1.2 and ends in a first second coupler 16a,16c,16e. The flow-through direction of the first check valve 42a,42a1,42a2 is towards the first flow control valve CV1,CV1.1,CV1.2, so that back-flow into the main conduit 14 cannot take place. The second branch conduit C2,C2.1,C2.2 has a second check valve 43a,43a1, 43a2 and ends in a second second coupler 16b,16d,16f. The flow-through direction of the second check valve 43a,43a1, 43a2 is towards the main conduit 14. A diversion conduit DC1,DC2,DC3 is connected to the first branch conduit C1,C1.1,C1.2 between the first check valve 42a,42a1,42a2 and the flow control valve CV1,CV1.1,CV1.2 and ends in a third second coupler 16g,16h,16i. A second flow control valve CV2,CV2.1,CV2.2 is provided in the diversion conduit DC1,DC2,DC3.

The dispensing lines 6a',6a"; 6'b,6b"; 6c',6c" of the CIP-system 1a have a first dispensing line part 6a',6b',6c' that has the take-off ends 7a',7b',7c' with the first couplers 8a,8b,8c. The end of the first dispensing line part 6a',6b',6c' opposite the take-off ends 7a',7b',7c' is an intermediate coupling end provided with another first coupler 8a',8b',8c' configured to couple to the third second coupler 16g,16h,16i of the flow distribution unit 13',13.1',13.2'.

A second dispensing line part 6a",6b",6c" has the dispenser ends 7a,7b,7c connected to the dispenser 5a,5b,5b. The end of the second dispensing line part 6a",6b",6c" opposite the dispenser ends 7a,7b,7c has yet another first coupler 8a", 8b", 8c". The second dispensing line part 6a', 6b', 6c' couples the dispenser 5a,5b,5c in liquid communication with the flow distribution unit 13',13.1',13.2', and the first dispensing line part 6a',6b',6c' couples the take-off receptacles 2a,2b,2c in liquid communication with the flow distribution unit 13',13.1',13.2'.

So irrespective of whether it is the content of the take-off receptacles 2a,2b,2c, the cleaning water or the ozonated water the liquid flows through the modified flow distribution unit 13',13.1',13.2'.

In the mode seen in FIG. 11 the CIP-system 1a is in operation to disinfect the first dispensing line part 6a',6b',6c' and the dispensers 5a,5b,5c with ozonated water supplied via ozonated water valve OWV. The first check valve 42a,42a1,42a2 and the flow control valve CV1,CV1.1, CV1.2 are open and allows the ozonated water to pass through the first dispensing line part 6a',6b',6c' and the dispensers 5a,5b,5c. In the mode seen in FIG. 11 the second flow control valve CV2,CV2.1,CV2.2 is closed and the second dispensing line part 6a", 6b", 6c" is not being disinfected. The same procedure can be made with cleaning water and flushing with ozonated water and cleaning water can be repeated as long as needed to satisfy cleaning and disinfecting requirements, such as bacterial count criteria.

After a satisfactory cleaning and/or disinfecting the ozonated water valve and the water valve are closed. Then the second flow control valve CV2,CV2.1,CV2.2 is opened (not shown) thereby allowing the content of the take-off receptacles 2a,2b,2c to flow via the first dispensing line part 6a',6b',6c' through interconnected another first coupler 8a', 8b',8c' and third second coupler 16g,16h,16i through open second flow control valve CV2,CV2.1,CV2.2 and diversion conduit DC1,DC2,DC3. From the diversion conduit DC1, DC2,DC3 the flow is diverted into the first branch conduit C1,C1.1,C1.2 and passes through the flow control valve CV1,CV1.1,CV1.2, out through interconnected first second coupler 16a,16c,16e and the yet another first coupler 8a' ',8b' ',8c" into the second dispensing line part 6a',6b',6c' and out of the dispensers 5a,5b,5c in response to opening said dispensers 5a,5b,5c, as shown with arrows A.

Due to each dispensing line having a modified flow distribution unit 13',13.1',13.2' with a more complex valve system than the valve system of the first embodiment of a flow distribution unit 13,13.1,13.2 of the first embodiment of a CIP-system 1 the second embodiment of a CIP-system 1a makes it possible to clean selected dispensing lines simultaneously with the remaining dispensing lines being in operative dispensing mode. Remotely placed take-off receptacles 2a,2b,2c may have really long second dispensing line parts 6a", 6b", 6c", which according to the second embodiment of a CIP-system 1a can be cleaned and disinfected in response to instructions from another location remote from the location of the take-off receptacles 2a,2b,2c, which makes the CIP-system 1a substantially automatic in respect of cleaning the second dispensing line parts 6a",6b",6c", thus the majority of the dispensing lines 6a, 6b, 6c.

The first dispensing line part 6a',6b',6c' are however not cleaned in FIG. 11. The way to get the first dispensing line part 6a',6b',6c' cleaned is illustrated in FIG. 12, which differs from FIG. 11 in that the first coupler 8a,8b,8c has been moved and coupled to the second second coupler 16b,16d, 16f. Ozonated water can the flow into diversion conduit DC1,DC2,DC3 and proceed via the interconnected another first coupler 8a',8b',8c' and the third second coupler 16g, 16h,16i through the looping first dispensing line part 6a', 6b',6c' via interconnected first coupler 8a,8b,8c and second second coupler 16b,16d,16f into the second branch conduit C2,C2.1,C2.2 for being recycled into the main conduit 14 via the second check valve 43a,43a1,43a2. At the same time the second dispensing line part 6a",6b",6c" is disinfected by the ozonated water or cleaned by cleaning water, as described above to conduct a full cleaning. Thus all first couplers, second couples, flow distributions units and dispensing lines are cleaned in this semi-automatic procedure.

In FIG. 12 all flow control valves CV1,CV1.1,CV1.2; CV2,CV2.1,CV2.2 are open to enable cleaning and disinfecting also the first coupler 8a,8b,8c and the first dispensing line part 6a',6b',6c'. The recycle valve RV is closed in FIG. 12, but it can be opened to let residual ozonated water or cleaning water flowing in the main conduit 14 out of the outlet end 14' to escape via the last flow distribution unit 13.2" in the series.

FIG. 13 shows a third embodiment of a CIP-system 1b, which is a modification of the second embodiment of an automatic and/or semi-automatic CIP-system 1a, as well as a modification of the first embodiment of an automatic and/or semi-automatic CIP-system 1a. For like parts same reference numerals are used.

In the third embodiment of a CIP-system 1b the first dispensing line part 6a',6b',6c', including the first coupler 8a,8b,8c at the take-off end 7a',7b',7c', and the yet another first coupler 8a",8b",8c" at the opposite end, is intended cleaned and disinfected in a separate process disconnected from the CIP-system 1b, thus without major stops in operation of the dispensing system but subject to manual replacement. So when the need for cleaning and disinfecting of a soiled first dispensing line part 6a',6b',6c' arises, said first dispensing line part 6a',6b',6c' with associated first couplers

8*a*,8*b*,8*c*; 8*a*",8*b*",8*c*" is simply replaced with a another clean and disinfected first dispensing line part 6*a*',6*b*',6*c*' having similar first couplers 8*a*,8*b*,8*c*; 8*a*",8*b*",8*c*" at opposite ends. The first dispensing line part 6*a*',6*b*',6*c*', the first coupler 8*a*,8*b*,8*c*, and the yet another first coupler 8*a*",8*b*", 8*c*" can then be cleaned and disinfected when the time is convenient, and be reused after appropriate cleaning and disinfecting.

The flow distribution unit 13",13.1",13.2" of the third embodiment of a CIP-system 1*b* is a third embodiment of a flow distribution unit 13",13.1",13.2", which differs in the configuration of the third embodiment of a flow distribution unit 13',13.1',13.2' in that a first flow control valve CV1; CV1.1; CV2.1 is disposed in the main conduit 14 upstream the junction C1*b*; C1*b*'; C1*b*" between the main conduit 14 and the first branch conduit C1; C1.1; C1.2 of the flow distribution unit 13",13.1",13.2", and a second flow control valve CV2; CV1.2; CV2.2 is disposed in the main conduit 14 downstream a junction C2*b*; C2*b*'; C2*b*;" between the main conduit 14 and the second branch conduit C2; C2.1; C2.2 of said flow distribution unit 13",13.1",13.2".

In the mode seen in FIG. 13 the second control valve CV2; CV21; CV2.2 at the second branch conduit C2; C2'; C2" is closed, and ozonated water flows via the main conduit 14 through the first branch conduit C1; C1'; C1" and into the second dispensing line part 6*a*",6*b*",6*c*" and out of dispensers 5*a*,5*b*,5*c*. The first dispensing line part 6*a*',6*b*',6*c*' is not being disinfected.

Once the cleaning and/or disinfecting has been completed the third embodiment of a CIP-system is put in a dispensing mode (not shown) by the electronic control system 17. In the dispensing mode the first flow control valve CV1; CV1.1; CV2.1 is closed and the second flow control valve CV2; CV1.2; CV2.2 is opened, whereby dispensing of the content in the take-off receptacle 2*a*,2*b*,2*c*, such as beer, can start being dispensed. In response to opening a dispenser sid content will be drawn into the first dispensing line part 6*a*',6*b*',6*c*', through interconnected another first coupler 8*a*', 8*b*',8*c*' and second coupler 16*b*,16*d*,16*f* into the second branch conduit C2; C2.1; C2.2 and through check valve 43*a*; 43*a*1; 43*a*.2 back through the segment of the main conduit 14 extending in the flow distribution unit 13; 13.1; 13.2 and further into the first branch conduit C1; C1.1; C1.2. Then the flowing content leaves the flow distribution unit 13; 13.1; 13.2 via interconnected yet another first coupler 8*a*",8*b*",8*c*" and second coupler 16*a*,16*c*,16*e* wherefrom the content flows into the second dispensing line part 6*a*",6*b*",6*c*" and out of dispensers 5*a*,5*b*,5*c*. The electronic control system 17 is responsible for operating the flow control valves.

The automatic or semi-automatic Clean-In-Place system and method of the present invention provides a proper solution and procedure for cleaning and disinfecting dispensing lines thereby preventing the buildup of organic material and mineral deposits while eliminating flavor changing microbes. Together with a well-designed and diligently maintenance plan to be executed by the electronic control system for operating and controlling the cleaning a trouble-free draught beer dispensing system is ensured in operation to dispense fresh, flavorful draught beer.

Contrary to many other chemical sanitizers, ozone is more efficient at lower temperatures because its stability increases. So when the ozonated water flows through the cooled draught beer dispensing lines the ozonated water is inherently cooled, thus applied cold, whereby the concentration of dissolved ozone in the ozonated water remains high during the entire cooled flow path to the discharge of the at least one dispensing lines, whereby energy costs can be substantially reduced, and disinfecting efficiency be exceptionally high and reliable.

The invention claimed is:

1. An automatic or semi-automatic Clean-In-Place system adapted for cleaning and disinfecting at least one dispensing line between a take-off station comprising at least one take-off receptacle and a dispensing station comprising at least one dispenser, wherein a dispensing line has a take-off end provided with a first coupler configured to couple to the take-off receptacle, and an opposite dispenser end adapted to be connected to a dispenser, a source of ozonated water connected to an ozonated water conduit, and a source of cleaning water (CW) connected to a water conduit, wherein the automatic or semi-automatic Clean-In-Place system comprises an ozonated water valve (OWV) inserted in the ozonated water conduit, a water valve (WV) inserted in the water conduit, a main conduit configured to in turns receiving water from the water conduit and ozonated water from the ozonated water conduit, the main conduit extends into a first plurality of n>1 serially arranged flow distribution, wherein a flow distribution unit of the first plurality of flow distribution units comprises a second plurality of m≥2 serially arranged branch conduits on the main conduit, at least one of the at least two branch conduits has at least one flow control valve disposed between a free branch end and its junction from the main conduit, and a second coupler provided at the free branch end, which second coupler is adapted to couple in fluid communication with the first coupler, and an electronic control system configured to operate and control at least operative status of the ozonated water valve (OWV), the water valve (WV) and the flow control valve, wherein:

the source of ozonated water is an electrolytic ozone generator configured to produce ozonated water on demand at a concentration of dissolved ozone in the ozonated water of at least 5 ppm, by electrolysis of water from a water supply (CW).

2. An automatic or semi-automatic Clean-In-Place system according to claim 1, wherein the electronic control system is configured to in turns, and in any selected order and number of times, operate and control the ozonated water valve (OWV), the water valve (WV) and the flow control valve to convey water through the at least one dispensing line in a water cleaning period (T2) to flush said dispensing line, and convey ozonated water to said at least one selected dispensing line in an ozonated water disinfection period (T1) to disinfect said dispensing line.

3. An automatic or semi-automatic Clean-In-Place system according to claim 1, wherein the water supply (CW) to the electrolytic ozone generator is the cleaning water supply (CW), preferably the water supply (CW) to the electrolytic ozone generator is filtered water from the cleaning water supply (CW), preferably the cleaning water supply (CW) is tap water.

4. An automatic or semi-automatic Clean-In-Place system according to claim 1, wherein an outlet end (14') of the main conduct at the n'th of the serially arranged flow distribution units is coupled in recycling fluid communication with the source of ozonated water or with the ozonated water conduit via a recycle valve (RV) configured to be closed when at least one of the water valve (WV), the ozonated water valve (OWV) and the flow control valve are open, and can be opened by the electronic control system when at least some of the flow control valves are closed, preferably when all flow control valves are closed.

5. An automatic or semi-automatic Clean-In-Place system according to claim 1 comprising:

- a flow sensor (F) provided in one or more of the main conduit and/or one or more of the branch conduits, and/or
- a pressure sensor (P) provided in one or more of the main conduit and/or one or more of the branch conduits,
- or combinations thereof,
- which sensors (F,P) are operatively coupled to the electronic control system.

6. An automatic or semi-automatic Clean-In-Place system according to claim 1, comprising a drain manifold (20) having a plurality of discharge hoses corresponding to the plurality of dispensing lines to be cleaned, which discharge hoses discharge into a common drain hose.

7. An automatic or semi-automatic Clean-In-Place system according to claim 1, wherein the system is configured to during cleaning the dispensers discharge directly into a drain, such as a sewer, sink, floor drain, or a discharge tray of the dispensing station, or a remote drain facility.

8. An automatic or semi-automatic Clean-In-Place system according to claim 1, comprising at least one check valve inserted in one or more of the branch conduits, the main conduit, the ozonated water conduit, the water conduit and the recycle conduit.

9. An automatic or semi-automatic Clean-In-Place system according to claim 1, wherein at least said main conduit, said branch conduits, said second coupler and said valves (OWV, CV1,CV2; CV1.1,CV2.1; CV1.2,CV2.2; RV42*a*,43*a*; 42*a*1, 43*a*1; 42*a*2,43*a*2) of the Clean-In-Place system (1; 1*a*; 1*b*) are manufactured of ozone resistant material, preferably the ozone resistant material is selected from the group of materials comprising stainless steel 316, stainless steel 304, ceramics, polyvinyl chloride (PVC), polyethylene (PE), polycarbonate (PC), polytetrafluoroethylene PTFE, Teflon, silicone, and/or titanium.

10. An automatic or semi-automatic Clean-In-Place system according to claim 1, wherein the system is configured to, when in use, to provide a concentration of dissolved ozone in the ozonated water for disinfecting a draught beer dispensing line of at least 8 ppm, more preferred at least 10 ppm.

11. An automatic or semi-automatic Clean-In-Place system according to claim 1, wherein the system when in use is configured to comprise an ozonated water disinfection period (T1) for disinfecting a draught beer dispensing line lasting between 5 and 20 minutes, preferably between 5-15 minutes, more preferred between 6-10 minutes.

12. An automatic or semi-automatic Clean-In-Place system according to claim 1, comprising an electronic control switch adapted to verify that the first coupler and the second coupler are coupled fluid-tight together.

13. An automatic or semi-automatic Clean-In-Place system according to claim 1, wherein the electronic control system is configured to be operated over a wireless network.

14. An automatic or semi-automatic Clean-In-Place system according to claim 1, characterized in being modified so that at least one flow control valve of a flow distribution unit is disposed in the main conduit upstream a junction between the main conduit and a first branch conduit of the flow distribution unit, and at least one flow control valve of a flow distribution unit is disposed in the main conduit downstream a junction between the main conduit and a second branch conduit of the flow distribution unit.

15. An automatic or semi-automatic Clean-In-Place system (1*a*) according to claim 1, wherein a diversion conduit (DC1; DC2; DC3) provides liquid communication between a first second coupler (16*a*, 16*c*, 16*e*) of the flow distribution unit (13",13.1",13.2") and at least one of the subsequent second couplers (16*g*,16*e*,16*i*) in series with the first second coupler of the flow distribution unit (13'; 13.1'; 13.2').

16. A method of cleaning and disinfecting a system of dispensing lines between a take-off station and a dispensing station (3), wherein providing the automatic or semi-automatic Clean-In-Place system according to claim 1, and performing the steps of

- a) disconnecting the selected one or more first couplers at the end of the respective dispensing lines from their respective take-off receptacle,
- b) coupling a second coupler to each of the free first couplers,
- c) opening the dispensers associated with the respective dispensing line,
- d) operating the electronic control system to operate at least the ozonated water valve (OWV), the water valve (WV) and the flow control valve to conduct a disinfection cycle including:
- d1) opening a selected number of flow control valves,
- d2) opening the water valve (WV) and flushing the associated dispensing lines between the first coupler and a discharge opening of the dispenser associated with the dispensing line with water in a water cleaning period (T2),
- d3) closing the water valve (WV),
- d4) opening the ozonated water valve (OWV) and disinfecting, in an ozonated water disinfection period (T1), the dispensing line between the first coupler and the discharge opening of the dispenser with ozonated water produced by an electrolytic ozone generator configured to produce ozonated water on demand by electrolysis of water from a water supply (CW),
- d5) closing the ozonated water valve (OWV),
- d6) optionally repeating steps d2) and d3); or optionally repeating steps d2) to d5),
- e) closing the flow control valves, and
- f) optionally disconnecting the first coupler and the second coupler.

17. A method according to claim 16, wherein the method further comprises step b1) between step b) and c), wherein step b1) comprises coupling a drain hose to a discharge opening of a dispenser, and step j), which is performed after step i), wherein step j) comprises decoupling the drain hose of the discharge opening of the dispenser.

18. A method according to claim 16, wherein the method further comprises an additional step of recycling residual produced ozonated water to any of the ozonated water source, the ozonated water conduit or a drain facility at the latest after step e).

19. A method according to claim 16, wherein the method further comprises an additional step of flushing the dispensing line with the content of the take-off receptacles.

20. A method according to claim 16 wherein the method further comprises one or more of in step d) adjusting the temperature of water supplied to the electrolytic ozonated water generator to between 20° C.-25° C. during electrolysis, and cooling the produced ozonated water using a cooling facility of the at least one dispensing line.

21. A draught beer system comprising the automatic or semi-automatic Clean-In-Place system according to claim 1 wherein the take-off receptacle is a keg, optionally a beer keg,
the dispensing station is a dispensing tower,
the dispenser is a draught beer faucet, and
the first coupler is a keg coupler.

* * * * *